United States Patent
Dubé et al.

(10) Patent No.: US 9,463,181 B2
(45) Date of Patent: *Oct. 11, 2016

(54) DOXEPIN ISOMERS AND ISOMERIC MIXTURES AND METHODS OF USING THE SAME TO TREAT SLEEP DISORDERS

(71) Applicants: Pernix Sleep Inc., Morristown, NJ (US); ProCom One, Inc., San Marcos, TX (US)

(72) Inventors: Susan E. Dubé, Carlsbad, CA (US); Neil B. Kavey, Chappaqua, NY (US)

(73) Assignees: Pemix Sleep, Inc., Morristown, NJ (US); ProCom One, Inc., San Marcos, TX (US)

( * ) Notice: Subject to any disclaimer, the term of this patent is extended or adjusted under 35 U.S.C. 154(b) by 365 days.

This patent is subject to a terminal disclaimer.

(21) Appl. No.: 13/692,415

(22) Filed: Dec. 3, 2012

(65) Prior Publication Data

US 2013/0102658 A1    Apr. 25, 2013

Related U.S. Application Data

(63) Continuation of application No. 12/535,640, filed on Aug. 4, 2009, now abandoned, which is a continuation-in-part of application No. 12/022,628, filed on Jan. 30, 2008, now abandoned, and a continuation-in-part of application No. 11/804,720, filed on May 18, 2007, now Pat. No. 8,513,299.

(60) Provisional application No. 60/898,376, filed on Jan. 30, 2007, provisional application No. 60/801,824, filed on May 19, 2006, provisional application No. 60/833,319, filed on Jul. 25, 2006.

(51) Int. Cl.
*A61K 31/335*    (2006.01)

(52) U.S. Cl.
CPC .................................. *A61K 31/335* (2013.01)

(58) Field of Classification Search
CPC ...................................................... A61K 31/335
See application file for complete search history.

(56) References Cited

U.S. PATENT DOCUMENTS

| | | |
|---|---|---|
| 3,420,851 A | 1/1969 | Bloom et al. |
| 3,438,981 A | 4/1969 | Stach |
| 3,509,175 A | 4/1970 | Tretter |
| 4,110,438 A | 8/1978 | Gahwyler |
| 4,434,171 A | 2/1984 | Meüller |
| 4,833,154 A | 5/1989 | Jean-Louis et al. |
| 5,030,632 A | 7/1991 | Sterling |
| 5,116,852 A | 5/1992 | Gammans |
| 5,332,661 A | 7/1994 | Adamczyk et al. |
| 5,502,047 A | 3/1996 | Kavey |
| 5,585,115 A | 12/1996 | Sherwood et al. |
| 5,643,897 A | 7/1997 | Kavey |
| 5,725,883 A | 3/1998 | Staniforth et al. |
| 5,725,884 A | 3/1998 | Sherwood et al. |
| 5,733,578 A | 3/1998 | Hunter et al. |
| 5,741,524 A | 4/1998 | Staniforth et al. |
| 5,858,412 A | 1/1999 | Staniforth et al. |
| 5,866,166 A | 2/1999 | Staniforth et al. |
| 5,948,438 A | 9/1999 | Staniforth et al. |
| 5,965,166 A | 10/1999 | Hunter et al. |
| 6,103,219 A | 8/2000 | Sherwood et al. |
| 6,106,865 A | 8/2000 | Staniforth et al. |
| 6,211,229 B1 | 4/2001 | Kavey |
| 6,217,907 B1 | 4/2001 | Hunter et al. |
| 6,217,909 B1 | 4/2001 | Sherwood et al. |
| 6,219,674 B1 | 4/2001 | Classen |
| 6,344,487 B1 | 2/2002 | Kavey |
| 6,358,533 B2 | 3/2002 | Sherwood et al. |
| 6,391,337 B2 | 5/2002 | Hunter et al. |
| 6,395,303 B1 | 5/2002 | Staniforth et al. |
| 6,403,597 B1 | 6/2002 | Wilson et al. |
| 6,407,128 B1 | 6/2002 | Scaife et al. |
| 6,471,994 B1 | 10/2002 | Staniforth et al. |
| 6,521,261 B2 | 2/2003 | Sherwood et al. |
| 6,584,472 B2 | 6/2003 | Classen |
| 6,683,102 B2 | 1/2004 | Scaife et al. |
| 6,746,693 B2 | 6/2004 | Staniforth et al. |
| 6,852,336 B2 | 2/2005 | Hunter et al. |
| 6,858,231 B2 | 2/2005 | Sherwood et al. |
| 6,866,867 B2 | 3/2005 | Staniforth et al. |
| 6,936,277 B2 | 8/2005 | Staniforth et al. |
| 5,502,047 C1 | 4/2006 | Kavey |
| 7,135,196 B2 | 11/2006 | Stockham |
| 7,179,488 B2 | 2/2007 | Sherwood et al. |

(Continued)

FOREIGN PATENT DOCUMENTS

| | | |
|---|---|---|
| WO | WO 99/40898 | 8/1999 |
| WO | WO 00/10554 | 3/2000 |

(Continued)

OTHER PUBLICATIONS

Office Actions and Responses in U.S. Appl. No. 12/301,223.
Abernethyl et al., Absolute bioavailability of imipramine: Influence of food, Psychopharmacology (Berl), 1984; 83(1):104-106.
ABPI (Association of the British Pharmaceutical Industry) Compendium of Data Sheets & SmPC's, 1999-2000; Pfizer Limited, p. 1158.
ABPI (Association of the British Pharmaceutical Industry) Compendium of Data Sheets and Summaries of Product Characteristics, 1996-1997; Pfizer Limited, p. 751-752.
ABPI (Association of the British Pharmaceutical Industry) Data Sheet Compendium 1991-1992; Pfizer Limited, p. 1147-1149.
ABPI (Association of the British Pharmaceutical Industry) Data Sheet Compendium 1993-1994; Pfizer Limited, p. 1205-1207.

(Continued)

*Primary Examiner* — Sarah Pihonak
(74) *Attorney, Agent, or Firm* — Servilla Whitney LLC

(57) ABSTRACT

The invention relates to use of the cis-(Z) isomer or isomeric mixtures containing specified ratios of the cis-(Z) and trans-(E) isomers of doxepin, metabolites of doxepin, pharmaceutically-acceptable salts of doxepin and prodrugs of the same; compositions containing the same, for the treatment of sleep disorders.

14 Claims, No Drawings

(56) References Cited

U.S. PATENT DOCUMENTS

| | | | |
|---|---|---|---|
| 7,276,536 | B2 | 10/2007 | Urata et al. |
| 7,452,872 | B2 | 11/2008 | Johnson |
| 7,915,307 | B2 | 3/2011 | Casseday et al. |
| 8,097,625 | B2 | 1/2012 | Lalji et al. |
| 2002/0037828 | A1 | 3/2002 | Wilson et al. |
| 2002/0197235 | A1 | 12/2002 | Moran |
| 2003/0206978 | A1 | 11/2003 | Sherwood et al. |
| 2003/0235617 | A1 | 12/2003 | Martino et al. |
| 2004/0063721 | A1 | 4/2004 | Deecher et al. |
| 2004/0115142 | A1 | 6/2004 | Sherwood et al. |
| 2004/0224017 | A1 | 11/2004 | Mulye |
| 2004/0265374 | A1 | 12/2004 | Staniforth et al. |
| 2005/0013861 | A1 | 1/2005 | Sherwood et al. |
| 2005/0118261 | A1 | 6/2005 | Oien et al. |
| 2005/0123609 | A1 | 6/2005 | Hirsh et al. |
| 2005/0147673 | A1 | 7/2005 | Staniforth et al. |
| 2005/0171160 | A1 | 8/2005 | Edgar et al. |
| 2005/0196439 | A1 | 9/2005 | Sherwood et al. |
| 2005/0214365 | A1 | 9/2005 | Yousef et al. |
| 2005/0239838 | A1 | 10/2005 | Edgar et al. |
| 2005/0256165 | A1 | 11/2005 | Edgar et al. |
| 2006/0008522 | A1 | 1/2006 | Staniforth et al. |
| 2006/0228487 | A1 | 10/2006 | Schaible |
| 2007/0281990 | A1 | 12/2007 | Rogowski et al. |
| 2008/0058407 | A1 | 3/2008 | Baron et al. |
| 2008/0058408 | A1 | 3/2008 | Rogowski et al. |
| 2008/0182890 | A1 | 7/2008 | Jochelson et al. |
| 2009/0042971 | A1 | 2/2009 | Rogowski et al. |
| 2009/0042972 | A1 | 2/2009 | Rogowski et al. |
| 2009/0074862 | A1 | 3/2009 | Schioppi et al. |
| 2010/0105614 | A1 | 4/2010 | Jochelson et al. |
| 2010/0179214 | A1 | 7/2010 | Dubèet al. |
| 2010/0179215 | A1 | 7/2010 | Dubè et al. |
| 2010/0227916 | A1 | 9/2010 | Kavey et al. |
| 2011/0077200 | A1 | 3/2011 | Jochelson et al. |
| 2011/0166215 | A1 | 7/2011 | Casseday et al. |
| 2011/0178166 | A1 | 7/2011 | Rogowski et al. |
| 2011/0318412 | A1 | 12/2011 | Schioppi et al. |
| 2012/0088822 | A1 | 4/2012 | Rogowski et al. |
| 2012/0245222 | A1 | 9/2012 | Rogowski et al. |
| 2013/0096188 | A1 | 4/2013 | Dube et al. |

FOREIGN PATENT DOCUMENTS

| | | |
|---|---|---|
| WO | WO 00/50025 | 8/2000 |
| WO | WO 0139749 | 6/2001 |
| WO | WO 03/004009 | 1/2003 |
| WO | WO 03/047519 | 6/2003 |
| WO | WO 03/066029 | 8/2003 |
| WO | WO 2007/136845 | 11/2007 |
| WO | WO 2007/142810 | 12/2007 |
| WO | WO 2007/142811 | 12/2007 |

OTHER PUBLICATIONS

ABPI (Association of the British Pharmaceutical Industry) Data Sheet Compendium 1994-1995; Pfizer Limited, p. 1150-1151.
ABPI (Association of the British Pharmaceutical Industry) Data Sheet Compendium 1995-1996; Pfizer Limited, p. 1239-1240.
ABPI (Association of the British Pharmaceutical Industry) Data Sheet Compendium 1998-1999; Pfizer Limited, p. 970-971.
ABPI (Association of the British Pharmaceutical Industry) Medicines Compendium, 2002; Pfizer Limited, p. 1792-1793.
Adamzyk et al., Quantitative determination of E- and Z-doxepin and E- and Z-desmethyldoxepin by high-performance liquid chromatography. Ther Drug Monit. 17(4):371-6 (1995).
Adapin, Drug Side Effects, http://www.depression-guide.com/adapin.htm, 2005, 1-3.
Albemarle Pulmonary Medicine Associates, http://apma-nc.com/PatientEducation/INSOMNIA.HTM, 2000, pp. 1-4.
Ambien (Zolpidem Tartrate) tablets CIV. Highlights of Prescribing Information. Revised Jun. 2009. Sanofi-Aventis U.S. LLC. p. 1-18.
Ambien (Zolpidem Tartrate) tablets CIV. Prescribing Information. Revised Jun. 2008. Sanofi-Aventis U.S. LLC. p. 1-22.

Ambien CR (zolipidem tartrate extended-release). Highlights of Prescribing Information. Package Insert. Jan. 2008, Sanofi-Aventis U.S. LLC. p. 1-7.
Ambien CR (zolpidem tartrate extended release) tablets—CIV. Full Prescribing Information. Sep. 2009. Web download: Jul. 6, 2010. http://products.sanofi-aventis.us/ambien_cr/ambiencr.html. p. 1-32.
Ambien CR (zolpidem tartrate extended release). Healthcare Professional Information. Healthcare Professionals. Help your insomnia patients meet the day on. Web download: Jul. 6, 2010. http://www.ambiencr.com/hcp/zolpidem-tartrate.aspx. p. 1-2.
Ancoli-Israel et al., Identification and Treatment of Sleep Problems in the Elderly, Review Article, Sleep Medicine Reviews, 1(1): 3-17, (1997).
Anon, Quitaxon 10 mg cp pellic séc. [Online] (2006), XP002507206, Retrieved from the Internet: URL:http://www.vidal.fr/Medicament/quitaxon-14133.htm> [retrieved on Dec. 8, 2008].
Approval data of the German drug regulatory authorities. DIMDI: AMIS—Public Part (AJ29). German Institute of Medical Documentation and Information within the scope of the Federal Ministry of Health. Pfizer Pharma GmBH. Sinquan 10 mg; capsules, Sinquan 100; capsules; Sinquan 100 mg; capsules, Sinquan 25 Intramuscular; solution; Sinquan 25 mg; capsules, Sinquan 50 mg; capsules, Sinquan 75 mg; capsules. Retrieved Nov. 16, 2005 from https://gripsdb.dimdi.de/session/0511161521292992047/13docs.htm.
Badenhorst et al., Determination of doxepin and desmethyldoxepin in human plasma using liquid chromatography-tandem mass spectrometry. J Chromatogr B Biomed Sci Appl. 742(1):91-8 (2000).
Baldrick, Pharmaceutical excipient development: the need for preclinical guidance. Regul Toxicol Pharmacol. 32(2): 210-218 (2000).
Becker, Pharmacologic and Nonpharmacologic Treatments of Insomnia, Neurol Clin. 23: 1149-1163 (2005).
Biggs et al., Dosage schedule and plasma levels of doxepin and desmethyldoxepin. J Clin Psychiatry. 39(10):740-2 (1978).
Bogaert et al. Plasma levels of the cis- and trans-isomers of doxepin and desmethyldoxepin after administration of doxepin to patients. Arzneimittelforschung. 31(1):113-5 (1981).
Brunello et al., Effect of Some Tricyclic and Nontricyclic Antidepressants on [H]Imiipramine Binding and Serotonin Uptake in Rat Cerebral Cortex After Prolonged Treatment. Fundam Clin Pharmacol. 1: 327-333 (1987).
Brunswick et al. Relationship between tricyclic antidepressant plasma levels and clinical response in patients treated with desipramine or doxepin. Acta Psychiatr Scand. 67(6):371-7 (1983).
Bundgaard, Ed. Design of Prodrugs: Bioreversible derivatives for various functional groups and chemical entities, Elsevier, Amsterdam (1985). Chapter 1. p. 1-92.
Burch et al., Amitriptyline pharmacokinetics. A crossover study with single doses of amitriptyline and nortriptyline, Psychopharmacology (Berl), 1981; 74(1):35-42.
CBS.com, Ambien May Prompt Sleep-Eating; http://www.cbsnews.com/stories/2006/03/15/early show/health/ (2 pages).
Charman, Lipids, Lipophilic Drugs, and Oral Drug Delivery—Some Emerging Concepts. J Pharm Sci .89(8):967-78 (2000).
Chen, Sleep, Depression and Antidepressants, British Journal of Psychiatry, 135: 385-402, (1979).
Chloral Hydrate Drug Information, Professional. Chloral Hydrate (Systemic). Drug Information Online. Drugs.com. Web download: Jul. 6, 2010. http://www.drugs.com/mmx/chloral-hydrate.html. p. 1-15.
Claudino et al., Antidepressants for Anorexia Nervosa (Review). Cochrane Database Syst Rev., John Wiley & Sons, Ltd., 1:1-39 (2006).
Conn et al., Pattern of Use of Antidepressants in Long-Tern Care Facilities for the Elderly, Journal of Geriatric Psychiatry and Neurology, vol. 5:4, p. 228-232, (1992).
Declerck et al., Increase in Slow-wave Sleep in Humans with the Serotonin-S2 Antagonist Ritanserin. Curr Ther Res., 41(4): 427-432 (1987).
Desyrel—trazadone hydrochloride tablet. Bristol-Myers Squibb Company. Prescribing Information. Revised Feb. 2009. p. 1-9.

(56) References Cited

OTHER PUBLICATIONS

Deuschle et al., Doxepin and its Metabolites in Plasma and Cerebrospinal Fluid in Depressed Patients, Psychopharmacology, 131(1): 19-22, (1997).

Dilger et al. High-performance liquid chromatographic determination of trans-doxepin and desmethyldoxepin. Arzneimittelforschung. 38(10):1525-8 (1988).

Doxal. Lääkeopas. Retrieved Nov. 28, 2005 from http://www.coronaria.fi/www/mtv3/laakkeet.php?id=299.

Doxal. Lääkkeet. Retrieved Nov. 28, 2005 from http:www.tohtori.fi/laakkeet/tuote.php3?ID=412.

Doxepin. Find Treatment & Support. The most reliable cancer treatment information. Cancer.org. Web download: Jul. 6, 2010. http://www.cancer.org/docroot/CDG/content/CDG_doxepin.asp?internal=1. p. 1-6.

Dugovic et al., 5-HT2 Receptors could be Primarily Involved in the Regulation of Slow-wave Sleep in the Rat. Euro J Pharma., 137: 145-146 (1987).

Dunleavy et al., Changes During Weeks in Effects of Tricyclic Drugs on the Human Sleeping Brain, British Journal of Psychiatry, 120: 663-672, (1972).

Ebert et al., Treating insomnia: Current and investigational pharmacological approaches. Pharmacol Thera., 112(3): 612-629 (Mar. 2006).

Elavil—Amitriptyline Hydrochloride—amitriptyline hydrochloride tablet, film coated. Mutual Pharmceutical Company, Inc. Revised Sep. 2007. p. 1-9.

Ereshefsky et al., Pharmacokinetic factors affecting antidepressant drug clearance and clinical effect: evaluation of doxepin and imipramine—new data and review. Clin Chem. 34(5):863-80 (1988).

Erman et al., Comparative Efficacy of Zolpidem and Temazepam in Transient Insomnia, Human Psychopharma Clin Exp., 16: 169-176 (2001).

Faulkner et al., Comparative assays for doxepin and desmethyldoxepin using high-performance liquid chromatography and high-performance thin-layer chromatography. J Pharm Sci. 72(10):1165-7 (1983).

Faulkner et al., Multiple-dose doxepin kinetics in depressed patients. Clin Pharmacol Ther. 34(4):509-15 (1983).

FAVA, Weight Gain and Antidepressants. J Clin Psychiatry., (61 Suppl) 11: 37-41, (2000).

Fawcett et al., Review of the Results from Clinical Studies on the Efficacy, Safety and Tolerability of Mirtazapine for the Treatment of Patients with Major Depression J. Affective Disorders (1998) 51: 267-285.

Friedel et al. Relationship of blood levels of sinequan to clinical effects in the treatment of depression in aged patients. In. Mendels J, editor. Amsterdam: Excerpta Medica. p. 51-53 (1975).

Fulton et al., Assessment of the Antidepressant Activity of Dothiepin and its Metabolites by Preclinical Tests. J Affect Dis. 4: 261-269 (1982).

Georgotas et al., Response of Depressive Symptoms to Nortiptyline, Phenelzine and Placebo, Br. J. Psychiatry (1987) 151: 102-106.

German Federal Gazette (BAnz) No. 240 of Dec. 22, 1992, p. 9545 (vol. 44).

Ghabrial et al., Geometric isomerization of doxepin during its N-demethylation in humans. Drug Metab Dispos. 19(3):596-9 (1991).

Gillin et al., Successful Separation of Depressed, Normal, and Insomniac Subjects by EEG Sleep Data, Arch Gen Psychiatry, vol. 36, p. 85-90, (1979).

Green, Douglas O., Clinical importance of doxepin antidepressant plasma levels. J Clin Psychiatry. 39(5):481-2 (1978).

Grundstrom et al., Sedative Properties of Doxepin in Comparison with Diazepam, Psychopharmacology, 54: 165-169 (1977).

Guidance for Industry SUPAC-IR/MR: Immediate Release and Modified Release Solid Oral Dosage Forms—Manufacturing Equipment Addendum, Jan. 1999.

Hajak et al., Nocturnal Melatonin Secretion and Sleep after Doxepin Administration in Chronic Primary Insomnia, Pharmacopsychiatry 29: 187-192, (1996).

Halcion—Triazolam tablet. Pharmacia and Upjohn Company. Prescribing Information. Revised Jan. 2009. p. 1-10.

Haritos et al., Role of cytochrome P450 2D6 (CYP2D6) in the stereospecific metabolism of E- and Z-doxepin. Pharmacogenentics. 10(7):591-603 (2000).

Haritos et al., Stereoselective measurement of E- and Z-doxepin and its N-desmethyl and hydroxylated metabolites by gas chromatography-mass spectrometry. J Chromatogr B Biomed Sci Appl. 736(1-2):201-8 (1999).

Hartmann et al., The Effects of Long Term Administration of Psychotropic Drugs on Human Sleep: III. The Effects of Amitriptyline, Psychopharmacologia, 33: 185-202 (1973).

Hartmann, Peter M., Clinical Pharmacology—Miratzapine: A Newer Antidepressant, American Family Physician (1999) 1-5.

Hartter et al., The N-demethylation of the doxepin isomers is mainly catalyzed by the polymorphic CYP2C19. Pharm Res. 19(7):1034-7 (2002).

Haute Autorite De Sante (France): Avis Dec. 13, 2006 [Online] 2006, XP002507207; Retrieved from the Internet: URL:http://www.has-sante.fr/portail/jcms/c_475580/quitaxon> [retrieved on Dec. 8, 2008].

Heal et al., Comparative Pharmacology of Dothiepin, its Metabolites, and other Antidepressant Drugs. Drug Dev Res. 27: 121-135 (1992).

Hellberg et al., The Hydrolysis of the Prostaglandin Analog Prodrug Bimatoprost to 17-Phenyl-Trinor PGF2 by Human and Rabbit Ocular Tissue. J Ocul Pharmacol Ther., 19(2): 97-103 (2003).

Higuchi et al., Pro-Drugs as Novel Delivery Systems, A.C.S. Symposium Series, American Chemical Society; vol. 14, (1975)—Title Pages Only.

Hobbs, Distribution and Metabolism of Doxepin, Biochem. Pharmacol., 18(8): 1941-1954, (1969).

Hohagen et al., Treatment of Primary Insomnia with Trimipramine: An Alternative to Benzodiazepine Hypnotics? Eur Arch Psychiatry Clin Neurosci. 244(2): 65-72 (1994).

Hrdina et al., Antidepressant plasma levels and clinical response in depressed patients treated with oxaprotiline and doxepin. Int Clin Psychopharmacol. Jul.;3(3):205-14 (1988).

Hrdina et al., Cis- and trans-isomers of doxepin and desmethyldoxepin in the plasma of depressed patients treated with doxepin. Ther Drug Monit. 12(2):129-33 (1990).

Hsu et al., Low-Dose Doxepin in the treatment of primary insomnia, Sleep, 28: suppl, p. A50, (2005).

Jacobsen, Low-Dose Trazodone as a Hypnotic in Patients Treated with MAOIs and Other Psychotropics: A Pilot Study, Journal of Clinical Psychiatry, 51: 298-392 (1990).

Joyce et al., Doxepin plasma concentrations in clinical practice. Could there be a pharmacokinetic explanation for low concentrations? Clin Pharmacokinet. 10(4):365-70 (1985).

Kales et al., Effects of Sinequan on sleep of Insomniac Subjects, Sleep Study Abstracts, p. 93, (1972).

Kirchheiner et al., Contributions of CYP2D6, CYP2C9 and CYP2C19 to the biotransformation of E- and Z-doxepin in healthy volunteers. Pharmacogenetics. 12(7):571-80 (2002).

Kline et al., Doxepin and Desmethyldoxepin Serum Levels and Clinical Response. In: Gottschalk LA MM, editor. Pharmacokinetics of psychoactive drugs: blood levels and clinical response. New York: Spectrum Press. p. 221-28 (1976).

Krakowski. Seminar on Psychopharmacology—Auspices of Academy of Psychosomatic Medicine, Dec. 8-9, 1968 Freeport, Grand Bahama Island, Psychosomatics, pp. 7-63 (1968).

Laimer et al., Effect of Mirtazapine Treatment on Body Composition and Metabolism, J Clin Psychiatry, 67(3): 421-524 (2006).

Lapp, Chronic Fatigue Syndrome is a Real Disease, North Carolina Family Physician, 43:1, (1992).

Leucht et al., Doxepin plasma concentrations: is there really a therapeutic range? J Clin Psychopharmacol. 21(4):432-9 (2001).

Linnoila et al., Clomipramine and doxepin in depressive neurosis. Plasma levels and therapeutic response. Arch Gen Psychiatry. 37(11):1295-9 (1980).

(56) References Cited

OTHER PUBLICATIONS

Luchtefeld, Answers to the Most Common Questions Regarding Prescription Drugs—Safeguard Your Health, Jenry Consulting 1999, http://www.grandtimes.com/Answer_Drugs.html, 1-3.
Lunesta (Eszopiclone) Tablets 1 mg, 2 mg, 3 mg. Prescribing Information. Package Insert. Sepracor Inc. Jan. 2009. p. 1-2.
Luo et al., The Quaternary Ammonium-Linked Glucuronide of Doxepin: A Major Metabolite in Depressed Patients treated with Doxepin. Drug Metab Dispos., 19(3): 722-724, (1991).
Manning et al., Central Nervous System Effects of Meclizine and Dimenhydrinate: Evidence of Acute Tolerance to Antihistamines. J. Clin. Psychiatry 32:996-1002 (1992).
Masaki et al., Involvement of Hypothalamic Histamine H1 Receptor in the Regulation of Feeding Rhythm and Obesity, Diabetes 53(9): 2250-2260, (2004).
Masaki et al., The Hypothalamic H1 Receptor: A Novel Therapeutic Target for Disrupting Diurnal Feeding Rhythm and Obesity. Trends Pharmacol Sci. 27(5): 279-284, (2006).
Mayers et al., Antidepressants and their effect on sleep, Hum Psychopharmacol., 20(8): 533-559 (Dec. 2005).
Mealy et al., Drugs Under Development for the Treatment of Psychiatric Disorders. Drugs Fut. 31(3): 266-284 (2006).
Mercer et al., Dietary Induced Anorexia: A Review of Involvement of the Histominergic System, J Am Coll Nutr., 15(3): 223-230, (1996).
Midha et al., Stereoselective pharmacokinetics of doxepin isomers. Eur J Clin Pharmacol. 42(5):539-44 (1992).
Moody et al., Biotransformation of Doxepin by *Cunninghamella elegans*, Drug Metab Dispo., 27(10): 1157-1164, (1999).
Narasimhachari et al., N-Alkylation of Secondary Amine Tricyclic Antidepressants as a General Method for Their Quantitation by GC-MS-SIM Technique. Analytical Lett. 12(B1): 77-88 (1979).
National Academy of Sciences, Sleeping Pills, Insomnia, and Medical Practice, Institute of Medicine, 32-33,103,125,149,169,198, (1979).
Natrol Melatonin 3 mg. 60 Tablets. Dietary Supplement. Manufactured by Natrol, Inc. Label. p. 1-3.
Neubauer, Sleep Problems in the Elderly. Am Fam Physician. 59(9): 2551-2558 (May 1999).
New Drug Application 16-798 for Sinequan approved in 1978 (includes evaluation of insomnia indication on pp. 46-47, 54, 57, 59.
Newcomer et al., The Metabolic Effects of Antipsychotic Medications, Can J Psychiatry. 51(8): 480-491 (2006).
Nicholson et al., Modulation of sleep by trimipramine in man, European Journal of Clinical Pharmacol, 37: 145-150, (1989).
Nierenberg et al., Management of Monoamine Oxidase Inhibitor-Associated Insomnia with Trazodone, Journal of Clinical Psychopharmacol, vol. 9 No. 1, p. 42-45, (1989).
NyQuil Cold & Flu. Nightime Relief. Acetaminophen, Doxylamine, Dextromethorphan, Alcohyl 10%. 6 Fl Oz. Vicks Label. 2 pages.
NyQuil Oral. Drugs & Medications. WebMD. Web download: Jul. 6, 2010. http://www.webmd.com/drugs/drug-6104-NyQuil+Oral.aspx?drugid=6104&drugname=NyQuil+Oral&source=1. p. 1-3.
Nytol Oral. Drugs & Medications—WebMD. Web download: Jul. 6, 2010. http://www.webmd.com/drugs/drug-10538-Nytol+Oral.aspx?drugid=10538&drugname=Nytol+Oral&source=0. p. 1-2.
Nytol Quickcaps with Diphenhydramine HCl. Nightime Sleep-Aid. 72 Caplets. Label. 4 pages.
O'Brien et al., GLC determination of doxepin plasma levels. J Pharm Sci. 65(7):1068-9 (1976).
Ookuma et al., Evidence for Feeding Elicited Through Antihistaminergic Effects of Tricyclic Antidepressants in the Rat Hypothalamus. Psychopharmacology (Berl). 101(4): 481-485, (1990).
Orthen-Gambill et al., Differential Effects of Psychotropic Drugs on Feeding in Rats: Is Histamine Blockade Involved? Pharmacol Biochem Behav., 36(4): 837-841 (1990).
Orthen-Gambill, Antihistaminic Drugs Increase Feeding, While Histidine Suppresses Feeding in Rats, Pharmacol Biochem Behav., 31(1): 81-86, (1988).

Pälvimäki et al. Interactions of selective serotonin reuptake inhibitors with the serotonin 5-HT2C receptor. Phychopharmacology, 126(3): 234-240 (1996).
Patent Information Leaflet, Sinequan™ (doxepin), United Kingdom, p. 1-2 (2002).
Pecknold et al., Trimipramine, Anxiety, Depression and Sleep, Drugs, vol. 38: Suppl. 1, p. 25-31, (1989).
Pfizer, Chemist Review of NDA 17-516, Division of Neurophamacological Drug Products, Chemists Review #3, (1973).
Pharmaca Fennica. Published by the Finnish Centre for Medicine Information (Lääketietokeskus); SR Doxal; (1992).
Pharmaca Fennica. Published by the Finnish Centre for Medicine Information (Lääketietokeskus); SR Doxal; 612-613 (1988).
Pharmaca Fennica. Published by the Finnish Centre for Medicine Information (Lääketietokeskus); SR Doxal; 714 (1991).
Pharmaca Fennica. Published by the Finnish Centre for Medicine Information (Lääketietokeskus); SR Doxal; 738 (1993).
Pharmaca Fennica. Published by the Finnish Centre for Medicine Information (Lääketietokeskus); SR Doxal; 830 (1995).
Pharmaca Fennica. Published by the Finnish Centre for Medicine Information Lääketietokeskus); Ye R Doxal; 534-535 (2000).
Pharmaca Fennica. Published by the Finnish Centre for Medicine Information (Lääketietokeskus); SR Sinequan; 845-846 (1993).
Pharmassure. Standardized. Valerian. Herbal Supplement. Minimum 0.8% Valerenic Acids (2mg). 250 mg. 60 Softgel Capsules. Distributed by PharmAssure, Inc. Label. p. 1-4.
Phillips et al., Sleep Disorders in the Elderly, Sleep Medicine 2: 99-114 (2001).
Physician's Desk Reference, 1999 ed., Medical Economics Company, Montvale NJ pp. 539-541 (Trazadone).
Physician's Desk Reference, 2000 ed., Medical Economics Company, Montvale NJ pp. 2366-2367 (Doxepine HCI).
Physician's Desk Reference, 2000 ed., Medical Economics Company, Montvale NJ pp. 3323-3324 (Trimipramine maleate).
Physician's Desk Reference, 2000 ed., Medical Economics Company, Montvale NJ pp. 549-551 (Amitriptyline HCI).
Physicians Desk Reference, Litton Industries, p. 1211, 93, (1976).
Physicians' Desk Reference, p. 1310-1312, (1990).
Physicians' Desk Reference, p. 1849-1850, (1990).
Physicians' Desk Reference, p. 2434-2435, (1990).
Pinder et al., Doxepin up-to-date: a review of its pharmacological properties and therapeutic efficacy with particular reference to depression. Drugs. 13(3):161-218 (1977).
Polish Drug Application for Sinequan 10 mg capsules. 01474/93. p. 1-4 with attached Annex in 4 pages, 1993.
Polish Drug Application for Sinequan 25 mg capsules. 01475/93. p. 1-4 with attached Annex in 4 pages, 1993.
Pollack, Is Biotechnology Losing Its Nerve?, NY Times (Feb. 29, 2004), pp. 1-4.
Powell et al. Compendium of Excipients for Parenteral Formulations, PDA J Pharm Sci Technol. 52(2): 238-311 (1998).
Prakash et al. Deuterium Labelling of the Antidepressant Drug Doxepin for Disposition Studies in Human Subjects. J Lab Comp Radiopharma. 28(9): 1037-47 (1990).
Remington: The Science and Practice of Pharmacy, 21st Ed., Lippincott Williams & Wilkins (2006). Table of Contents Only.
Restoril—Temazepam capsule. Mallinckrodt Inc. Prescribing Information. Revised Mar. 2006. p. 1-8.
Ribbentrop et al., Pharmacologic studies of doxepin, an antidepressive agent with centrally anticholinergic and sedative effects. Arzneimittelforschung. 15:863-68 (1965). Translation of Abstract only.
Richardson et al., Tolerance to Daytime Sedative Effects of H1 Antihistamines. J Clin Psychopharmacol. 22(5): 511-515 (2002).
Richelson et al., Antagonism by Antidepressants of Neurotransmitter Receptors of Normal Human Brain in Vitro, J Pharmacol Exp Ther. 230(1): 94-102 (1984).
Richelson, Tricyclic Antidepressants and Histamine H1 Receptors, Mayo Clin Proc., 54:669-674, (1979).
Roche, Bioreversible Carriers in Drug Design: Theory and Application, Pergamon Press: New York, pp. 14-21 (1987)—Contents Pages Only.

(56) References Cited

OTHER PUBLICATIONS

Rosseel et al., Quantitative GLC determination of cis- and trans-isomers of doxepin and desmethyldoxepin. J Pharm Sci. 67(6):802-5 (1978).
Roth et al., Efficacy and Safety of doxepin 1, 3 , and 6mg in elderly adults with primary insomnia, Sleep (Rochester),29: suppl. S (2006).
Roth et al., Efficacy and Safety of Doxepin 1mg, 3mg , and 6mg in Adults with Primary Insomnia, Sleep, 30(11): 1555-1561 (Nov. 2007).
Roth et al., Efficacy and Safety of Zolpidem-MR: A Double-Blind, Placebo-Controlled Study in Adults with Primary Insomnia, Sleep Med. 7(5): 397-406 (2006).
Roth et al., Psychopharmacolodgy: The Effects of Doxepin HCI on Sleep and Depression, Journal of Clinical Psychiatry, 43:9, p. 366-368 (1982).
Rozerem (ramelteon) tablets. Highlights of Prescribing Information. Takeda Pharmaceuticals. Revised Oct. 2008. p. 1-6.
Saul, Stephanie, Study Links Ambien Use to Unconscious Food Forays, The New York Times http://www.nytimes.com/2006/03/14/health/14sleep.html (4 pages).
Scharf et al., Efficacy and Safety of Doxepin 1 mg, 3 mg, and 6 mg in Elderly Patients With Primary Insomnia: A Randomized, Double-Blind, Placebo-Controlled Crossover Study. J Clin Psychiatry 69(10): 1557-1564 (Oct. 2008).
Schatzberg et al., "Hypnotics" Manual of Clinical Psychopharmacology, American Psychiatric Press, Inc., Washington D.C., p. 173-189, (1986).
Schweitzer et al., Sleepiness and Performance During Three-Day Administration of Cetirizine or Diphenhydramine. J Allergy Clin Immunol. 94(4): 716-724 (1994).
Seifritz E. Contribution of Sleep Physiology to Depressive Pathophysiology, Neuropsychopharmacology 25(5) S1: S85-S88 (Nov. 2001).
Seminar on Psychosomatics, Auspices of Academy of Psychosomatic Medicine, p. 4-63 (1968).
Shu et al., The Identification of Urinary Metabolites of Doxepin in Patients. Drug Metabolism & Disposition, Drug Metabolism & Disposition, 18(5): 735-741 (1990).
Shu et al., Identification of Phenolic Doxepin Glucuronides from Patient Urine and Rat Bile. Drug Metab Disp. 18(6): 1096-1099 (1990).
Silenor (doxepin) Drug Description. RXList: Apr. 2, 2010. p. 1.
Silenor (doxepin) Prescribing Information. Revised Mar. 2010. p. 1-12.
Sinequan (doxepin HCI) Capsules Oral Concentrate. Prescribing Information. Revised Oct. 2008. p. 1-13.
Sinequan (Doxepin, Adapin): A guide to sinequan side effects. depression-guide.com. (2005). Web download: Jul. 6, 2010. http://www.depression-guide.com/sinequan.htm. p. 1-3.
Sinequan Dosage. eMEDTV. Clinaero, Inc. Updated/reviewed Apr. 2, 2007. Web download: Jul. 6, 2010. http://depression.emedtv.com/sinequan/sinequan-dosage.html. p. 1-2.
Sokoliess et al., Separation of (Z)- and (E)-isomers of thioxanthene and dibenz[b,e]oxepin derivatives with calixarenes and resorcinarenes as additives in nonaqueous capillary electrophoresis. Electrophoresis. 24(10):1648-57 (2003).
Somaxon Pharmaceuticals Announces Acceptance for Filing of New Drug Application for Silenor™ for the Treatment of Insomnia, Somaxon Pharmaceuticals Press Release, San Diego, CA, p. 1-5 (Apr. 15, 2008).
Somaxon Pharmaceuticals Announces Completion of 26-Week Transgenic Mouse Carcinogenicity Study of Silenor™, Somaxon Pharmaceuticals Press Release, San Diego, CA, p. 1-3 (Jan. 9, 2008).
Somaxon Pharmaceuticals Announces Data to be Presented at American Psychiatric Association 161st Annual Meeting, Somaxon Pharmaceuticals Press Release, San Diego, CA (May 2, 2008).
Somaxon Pharmaceuticals Announces Data to be Presented at American Psychiatric Association 161st Annual Meeting, Somaxon Pharmaceuticals Press Release, San Diego, CA, p. 1-7 (May 7, 2008).
Somaxon Pharmaceuticals Announces FDA Approval of Silenor® (Doxepin) for the Treatment of Insomnia, Somaxon Pharmaceuticals Press Release, San Diego, CA, p. 1-5 (Mar. 18, 2010).
Somaxon Pharmaceuticals Announces Positive Phase 3 Results with Silenor™ for theTreatment of Adults with Chronic Insomnia, Somaxon Pharmaceuticals, p. 1-5, (Apr. 10, 2006).
Somaxon Pharmaceuticals Announces Positive Results in a Phase II Dose-Finding Study of Low-dose Doxepin in Adults with Primary Sleep Maintenance Insomnia, Somaxon Pharmaceuticals, p. 1-2, (Jan. 6, 2005).
Somaxon Pharmaceuticals Announces Positive Results in a Phase II Dose-Finding Study of Low-Dose Doxepin in Elderly Patients with Primary Sleep Maintenance Insomnia, Somaxon Pharmaceuticals, p. 1-3, (Apr. 21, 2005).
Somaxon Pharmaceuticals Announces Presentation of Phase II Silenor® Data at the Associated Professional Sleep Societies Annual Meeting, Somaxon Pharmaceuticals, p. 1-2, (Jun. 20, 2006).
Somaxon Pharmaceuticals Announces the Completion of Enrollment in a Phase II Study Evaluating S0-101 for the Treatment of Sleep Maintenance Insomnia in Adults, Somaxon Pharmaceuticals, p. 1, (Oct. 7, 2004).
Somaxon Pharmaceuticals Presents Analyses of Silenor Clinical Data at the American Psychiatric Association Annual Meeting, Somaxon Pharmaceuticals Press Release, San Diego, CA, p. 1-6 (May 20, 2009).
Somaxon Pharmaceuticals Presents Pharmacological Data on Doxepin at the 21st European College of Neuropsychopharmacology Congress, Somaxon Pharmaceuticals Press Release, San Diego, CA, p. 1-3 (Sep. 2, 2008).
Somaxon Pharmaceuticals Provides Update on New Drug Application for Silenor® (Doxepin) for the Treatment of Insomnia, Somaxon Pharmaceuticals Press Release, San Diego, CA, p. 1-4 (Apr. 7, 2009).
Somaxon Pharmaceuticals Provides Update on New Drug Application for Silenor® for the Treatment of Insomnia, Somaxon Pharmaceuticals Press Release, San Diego, CA, p. 1-3 (Jan. 21, 2010).
Somaxon Pharmaceuticals Provides Update on Preclinical and Clinical Programs for Silenor™, Somaxon Pharmaceuticals Press Release, San Diego, CA, p. 1-3 (Sep. 11, 2006).
Somaxon Pharmaceuticals Provides Update on Silenor® Development Program for the Treatment of Insomnia, Somaxon Pharmaeuticals, p. 1-5, (Jul. 19, 2006).
Somaxon Pharmaceuticals Provides Update on Silenor™ Development Program, Somaxon Pharmaceuticals Press Release, San Diego, CA, p. 1-3 (May 9, 2007).
Somaxon Pharmaceuticals Provides Update on Silenor™ Preclinical Program, Somaxon Pharmaceuticals Press Release, San Diego, CA, p. 1-7 (Feb. 13, 2007).
Somaxon Pharmaceuticals Receives Complete Response Letter from the FDA for Silenor® (Doxepin), Somaxon Pharmaceuticals Press Release, San Diego, CA, p. 1-3 (Feb. 26, 2009).
Somaxon Pharmaceuticals Receives Complete Response Letter from the FDA for Silenor® NDA, Somaxon Pharmaceuticals Press Release, San Diego, CA, p. 1-3 (Dec. 7, 2009).
Somaxon Pharmaceuticals Resubmits New Drug Application for Silenor® (Doxepin) for the Treatment of Insomnia, Somaxon Pharmaceuticals Press Release, San Diego, CA, p. 1-4 (Jun. 4, 2009).
Somaxon Pharmaceuticals Scheduled to Meet with FDA to Discuss Complete Response Letter for Silenor® NDA, Somaxon Pharmaceuticals Press Release, San Diego, CA (Dec. 17, 2009).
Somaxon Pharmaceuticals' Silenor® Data Presented at the 22nd Annual Meeting of the Associated Professional Sleep Societies, Somaxon Pharmaceuticals Press Release, San Diego, CA, p. 1-4 (Jun. 12, 2008).
Somaxon Pharmaceuticals Submits New Drug Application for Silenor™ for the Treatment of Insomnia, Somaxon Pharmaceuticals Press Release, San Diego, CA, p. 1-6 (Jan. 31, 2008).

(56) References Cited

OTHER PUBLICATIONS

Somaxon Pharmaceuticals to Present Data at the 22nd Annual Meeting of the Associated Professional Sleep Societies, Somaxon Pharmaceuticals Press Release, San Diego, CA (Jun. 4, 2008).
Somaxon Pharmaceuticals, Inc. Initiates Phase III Clinical Trials of Silenor™ in Patients with Insomnia, Somaxon Pharmaceuticals Press Release, San Diego, CA, p. 1-3 (Jun. 9, 2005).
Somaxon Pharmaceuticals, Inc. Initiates Second Phase III Clinical Trials of Silenor™ Somaxon Pharmaceuticals Press Release, San Diego, CA (Sep. 20, 2005).
Somaxon Pharmaceuticals' Silenor™ Demonstrates Positive Results in a Phase 3 Transient Insomnia Clinical Trial, Somaxon Pharmaceuticals, p. 1-5, (Oct. 23, 2006).
Somaxon Pharmaceuticals' Silenor™ Demonstrates Positive Results in its Third Phase 3 Clinical Trial in Insomnia, Somaxon Pharmaceuticals, p. 1-6, (Nov. 20, 2006).
Somaxon Pharmaeuticals Announces the Completion of Enrollment in a Phase II Study Evaluating S0-101 for the Treatment of Sleep Maintenance Insomnia in Adults, Somaxon Pharmaceuticals, p. 1, (Oct. 7, 2004).
Somaxon's Silenor™ Demonstrates Positive Results in Long-Term Phase 3 Clinical Trial in Elderly Patients with Insomnia, Somaxon Pharmaceuticals, p. 1-7, (Dec. 18, 2006).
Sominex Caplets. Nightime sleep-aid—Diphenhydramine. GlaxoSmithKline. Consumer Healthcare, L.P. Label. 3 pages.
Sominex Oral. Drugs & Medications. WebMD. Web download: Jul. 6, 2010. http://www.webmd.com/drugs/drug-15470-Sominex+Oral.aspx?drugid=15470&drugname=Sominex+Oral&source=1. p. 1-3.
Sonata (Zaleplon) Capsules. Prescribing Information. King Pharmaceuticals. Feb. 2009. p. 1-15.
Sonata Official FDA information, side effects and uses. Drug Information Online. Drugs.com. Web. Jul. 6, 2010. http://www.drugs.com/pro/sonata.html. p. 1-22.
Stella et al.—Prodrugs: Challenges and Rewards, Part 1, Biotechnology: Pharmaceutical Aspects, p. 24, 2007.
Stimmel et al., Mirtazapine: An Antidepressant with Noradrenergic and Specific Serotonergic Effects Pharmacotherapy, (1997) 17(1): 10-21.
Summary Basis for approval of ADAPIN (1972) Pursuant to FOIA Request filed in 1981.
Summary Basis for approval of Sinequan® (1973) Pursuant to FOIA Request filed in 1973 (sedative, tranquilizer and sleep effects mentioned for example on pp. 50, 54-56, 58-59).
Technical Information/Summary of Drug Characteristics (SPC), Pfizer, p. 1-4, (2004).
Thase, Michael E., Antidepressant Treatment of the Depressed Patient with Insomnia, J. Clin. Psychiatry (1999) 60(Suppl. 17): 28-31.
Tylenol PM Extra Strength Pain Reliever. Nighttime Sleep Aid. Contains Acetaminophen, Diphenhydramine HCI. 24 Geltabs. Label. 4 pages.
Tylenol PM Oral. Drugs & Medications—WebMD. Web download: Jul. 6, 2010. http://www.webmd.com/drugs/drug-74986-Tylenol+PM+Oral.aspx?drugid=74986&drugname=Tylenol+PM+Oral&source=1. p. 1-3.
Tylenol PM. Extra Strength Pain Reliever. Nighttime Sleep Aid. Contains Acetaminophen, Diphenhydramine HCI. 50 Caplets. Label. 4 pages.
Vincent et al., Use of Human Sleep as a Test of Drug's Psychotropic Action with Doxepin as an example, Bordeaux Medical, No. 10, 2650-51, 2653-54, 2657-57, and 2661, (1971).
Virtanen et al., Radioimmunoassay for doxepin and desmethyldoxepin., Acta Pharmacol Toxicol (Copenh). 47(4):274-8 (1980).
Voshaar et al., Zolpidem is not Superior to Temazepam with Respect to Rebound Insomnia: A Controlled Study. Eur Neuropsychopharmacol. 14(4): 301-306 (2004).
Ward et al., Doxepin plasma levels and therapeutic response in depression: preliminary findings. J Clin Psychopharmacol. 2(2):126-8 (1982).
Ware, Tricyclic Antidepressants in the Treatment of Insomnia, Journal of Clinical Psychiatry, 44 [9, Section 2]: 25-28 (1983).
Wheatley, Prescribing Short-Acting Hypnosedatives: Current Recommendations from a Safety Perspective, Drug Safety 7(2):106-115 (1992).
Wolfe, Antidepressant Withdrawal Reactions. Am Fam Physician. 56(2): 455-462, (1997).
Wyatt et al., Carbon[13] NMR of Z- and E-Doxepin Hydrochloride. Applied Spectroscopy. 49(4):538-542 (1986).
Yan et al., Stereoselective and simultaneous measurement of cis- and trans-isomers of doxepin and N-desmethyldoxepin in plasma or urine by high-performance liquid chromatography. J Chromatogr B Biomed Sci Appl. 691(1):131-8 (1997).
Yan et al., Stereoselective in vivo and in vitro studies on the metabolism of doxepin and N-desmethyldoxepin. Xenobiotica. 27(12): 1245-1257 (1997).
Zaleplon Capsules. Drug Information Online. Drugs.com. Web download: Aug. 25, 2009. http://www.drugs.com/pro/zaleplon.html?printable=1. and Package Label. Augobindo Pharma Ltd. p. 1-23.
Ziegler et al., Doxepin kinetics. Clin Pharmacol Ther. 23(5):573-9 (1978).
Zimmermann et al., "Epidemiology, implications and mechanisms underlying drug-induced weight gain in psychiatric patients" J. Psychiatric Research (2003) 37: 193-220.
Zung, Effect of Antidepressant Drugs on Sleeping and Dreaming, Excerpta Medica Foundation International Congress Series, No. 150, 1824-1826, (1968).
International Search Report and Written Opinion dated Jan. 21, 2008 in PCT/US2007/012107, filed May 18, 2007.
International Preliminary Report on Patentability & Written Opinion dated Nov. 21, 2008 in PCT/US2007/012107, filed May 18, 2007.
International Search Report dated Dec. 10, 2007 in PCT/US2007/016464, filed Jul. 20, 2007.
International Preliminary Report on Patentability & Written Opinion dated Jan. 20, 2009 in PCT/US2007/016464, filed Jul. 20, 2007.
International Search Report dated Jan. 24, 2008 in PCT/US2007/012105, filed May 18, 2007.
International Preliminary Report on Patentability & Written Opinion dated Nov. 21, 2008 in PCT/US2007/012105, filed May 18, 2007.
International Search Report dated Jan. 24, 2008 in PCT/US2007/012106, filed May 18, 2007.
International Preliminary Report on Patentability & Written Opinion dated Nov. 21, 2008 in PCT/US2007/012106, filed May 18, 2007.
International Search Report dated Jun. 17, 2008 in PCT/US2007/080492, filed Oct. 4, 2007.
International Preliminary Report on Patentability & Written Opinion dated Apr. 7, 2009 in PCT/US2007/080492, filed Oct. 4, 2007.
International Search Report dated Aug. 11, 2007 in PCT/US2007/011893, filed May 18, 2007.
International Preliminary Report on Patentability dated Dec. 4, 2008 in PCT/US2007/011893, filed May 18, 2007.
International Search Report dated Mar. 18, 2008 in PCT/US2007/082569, filed Oct. 25, 2007.
Partial International Search Report dated Apr. 8, 2008 in PCT/US2007/082569, filed Oct. 25, 2007.
International Preliminary Report on Patentability dated May 7, 2009 in PCT/US2007/082569, filed Oct. 25, 2007.
International Search Report and Written Opinion dated Jul. 29, 2008 in PCT/US2007/086682, filed Dec. 6, 2007.
International Preliminary Report on Patentability and Written Opinion dated Jun. 18, 2009 in PCT/US2007/086682, filed Dec. 6, 2007.
International Search Report and Written Opinion dated Aug. 13, 2009 in PCT/US2009/042912, filed May 5, 2009.
Electronic File History of U.S. Appl. No. 11/781,165, filed Jul. 20, 2007 (U.S. Pat. No. 7,915,307, issued Mar. 29, 2011) containing Office Action(s) dated Oct. 14, 2008, Jul. 7, 2009, Sep. 29, 2009, Apr. 6, 2010, Oct. 21, 2010 and Nov. 12, 2010 and Applicant Response(s) filed Apr. 14, 2009, Dec. 4, 2009, Jul. 6, 2010 and Oct. 21, 2010 as of Sep. 14, 2012.

(56) References Cited

OTHER PUBLICATIONS

Electronic File History of U.S. Appl. No. 11/804,722, filed May 18, 2007 (Abandoned) containing Office Action(s) dated Jun. 15, 2010, Nov. 8, 2010 and Jun. 2, 2011 and Applicant Response(s) filed Oct. 15, 2010.
Electronic File History of U.S. Appl. No. 12/022,628, filed Jan. 30, 2008 containing Office Action(s) dated Mar. 6, 2009 and Nov. 20, 2009—abandoned.
Electronic File History of U.S. Appl. No. 12/022,788, filed Jan. 30, 2008 containing Office Action(s) dated Mar. 9, 2009 and Dec. 9, 2009—abandoned.
Electronic File History of U.S. Appl. No. 12/976,866, filed Dec. 27, 2010 (Abandoned) containing Office Action(s) dated Oct. 19, 2011 and Dec. 8, 2011 and Applicants Response filed Sep. 30, 2011.
Electronic File History of U.S. Appl. No. 11/867,595, filed Oct. 4, 2007 containing Office Action(s) dated Oct. 21, 2010, and May 10, 2011 and Applicants Response(s) filed Apr. 20, 2011, Sep. 30, 2011, Nov. 10, 2011 and Jul. 11, 2012 as of Sep. 26, 2012.
Council on Drugs, Evaluation of Doxepin Hydrochloride (Sinequan), JAMA, 215(12): 1967-68 (Mar. 22, 1971).
Pollack et al., The Selective GABA Reuptake Inhibitor Tiagabine for the Treatment of Generalized Anxiety Disorder: Results of a Placebo-Controlled Study, J Clin Psychiatry 66: 1401-1408 (Nov. 2005).
Rodenbeck et al., The sleep-improving effects of doxepin are paralleled by a normalized plasma cortisol secretion in primary insomnia, Psychopharma. 170(4): 423-428 (2003).
BPAI decision issued Dec. 11, 2012 in U.S. Appl. No. 11/804,720, filed May 18, 2007.
Electronic File History of U.S. Appl. No. 12/301,457, filed Apr. 12, 2010 containing Office Action(s) dated Jun. 7, 2012 and Applicants Response(s) filed Apr. 12, 2010 and Nov. 29, 2012 as of Dec. 17, 2012.
Electronic File History of U.S. Appl. No. 12/446,914, filed May 27, 2010 containing Office Action(s) dated Aug. 5, 2011, Jan. 20, 2012, Feb. 17, 2012 and Sep. 5, 2012 and Applicants Response(s) filed May 27, 2010, Jan. 20, 2012, and Aug. 17, 2012 as of Sep. 25, 2012.
Electronic File History of U.S. Appl. No. 13/007,334, filed Jan. 14, 2011 (Abandoned) containing Office Action(s) dated Apr. 17, 2012, as of Sep. 25, 2012.
Electronic File History of U.S. Appl. No. 12/102,985, filed May 6, 2011 (Abandoned) containing Office Action(s) dated Mar. 16, 2012 and Applicant(s) submissions Dec. 22, 2011 and Sep. 17, 2012 abandoned.
Electronic File History of U.S. Appl. No. 12/101,917, filed Apr. 11, 2008 containing Office Action(s) dated Oct. 21, 2010, May 10, 2011, Jan. 12, 2012 and Nov. 21, 2012 Applicants Response(s) filed Dec. 2, 2008, Dec. 29, 2011 and Jul. 30, 2012 as of Dec. 17, 2012.
Civil Docket of the U.S. District Court, District of Delaware, Case #1:11-cv-00537-RGA-MPT, printed Dec. 21, 2012 involving U.S. Pat. No. 6,211,229 and U.S. Pat. No. 7,915,307 of Somaxan Pharmaceuticals, Inc., pp. 1-5.
Japanese Office Action dated Aug. 27, 2012 in Application No. 2009-511109, filed May 18, 2007.
International Search Report and Written Opinion dated Jan. 19, 2008 in PCT/US2008/060131, filed Apr. 11, 2008.
International Preliminary Report on Patentability dated Oct. 13, 2009 in PCT/US2008/060131, filed Apr. 11, 2008.
Final Office Action in U.S. Appl. No. 14/804,595 dated Mar. 21, 2016, 10 pages.
Final Office Action in U.S. Appl. No. 13/692,715 dated Mar. 23, 2016, 19 pages.

US 9,463,181 B2

DOXEPIN ISOMERS AND ISOMERIC MIXTURES AND METHODS OF USING THE SAME TO TREAT SLEEP DISORDERS

RELATED APPLICATIONS

This application is a continuation of U.S. application Ser. No. 12/535,640, filed Aug. 4, 2009, which is a continuation-in-part of U.S. application Ser. No. 12/022,628, filed Jan. 30, 2008, which claims the benefit of, and priority to, U.S. Provisional Application No. 60/898,376, filed Jan. 30, 2007; and U.S. application Ser. No. 12/022,628 is a continuation-in-part of U.S. application Ser. No. 11/804,720, filed May 18, 2007, which claims priority to U.S. Provisional Application Nos. 60/801,824, filed May 19, 2006, and 60/833,319, filed Jul. 25, 2006. The entire content of all of these applications are incorporated herein by reference.

BACKGROUND OF THE INVENTION

1. Field of the Invention

The invention relates to use of the cis-(Z) isomer or isomeric mixtures containing specified ratios of the cis-(Z) and the trans-(E) isomers of doxepin and metabolites of doxepin, as well as pharmaceutically-acceptable salts and prodrugs of the same; and compositions containing the same, for the treatment of sleep disorders.

2. Description of the Related Art

Sleep is essential for health and quality of life. Insomnia is a subjective complaint of dissatisfaction with the quantity, quality or timing of sleep. Insomnia is estimated to occur in approximately 12% to 25% of the general population, although this is probably an underestimate as there is evidence that many adults do not report their sleep problems to a health care professional.

One study has found that fewer than 15% of those who suffer from insomnia are treated with prescription medications. Medications commonly used to treat sleep disorders such as insomnia, include sedative antidepressants, antipsychotics, antihistamines, melatonin receptor agonists, benzodiazepines, and non-benzodiazepine hypnotics.

Benzodiazepines work by binding to and activating sites on the GABA-A receptor complex. Short, intermediate and long-acting benzodiazepines such as triazolam, temazepam and flurazepam were all commonly prescribed for this indication. While these agents have proven to be efficacious and relatively safe, benzodiazepines are associated with a multitude of adverse effects, including residual daytime sedation ("hangover"), amnesia, memory loss and respiratory depression. Rebound insomnia has also been associated with benzodiazepines. Tolerance to the hypnotic effects of the benzodiazepines is common and abrupt discontinuation can result in withdrawal symptoms such as agitation, rebound insomnia, perceptual changes, confusion, disorientation and even seizures.

Non-benzodiazepine hypnotics have become the primary class of medications for the treatment of insomnia. The leading approved non-benzodiazepine insomnia medications, eszopiclone, zolpidem, and zaleplon, also work by binding to and activating the GABA-A receptors. All these drugs approved for the treatment of insomnia that act via the GABA-A receptor, including benzodiazepine and non-benzodiazepine hypnotics, have a potential for addiction and abuse and are classified as Schedule IV controlled substances by the U.S. Drug Enforcement Administration. As a result, many physicians are reluctant to prescribe, and patients are reluctant to take these drugs for chronic use in treating insomnia. The prescribing of a Schedule IV controlled substance brings scrutiny from the Drug Enforcement Administration and other regulatory bodies, and requires registration and administrative controls in physicians' offices.

Also, the sedative antidepressants account for a large percentage of the total prescriptions written for insomnia. The National Disease and Therapeutic Index estimates that more than 60% of the 13 million annual trazodone prescriptions are written for the treatment of insomnia, even though trazodone is not indicated for that usage and has never been promoted for that condition. Although there are very limited data to support the use of trazodone for insomnia and it is associated with undesirable side effects, trazodone is often prescribed because it is a non-scheduled agent, meaning non-addictive, unlike the benzodiazepines and other GABA-receptor agonists which are approved for the treatment of insomnia.

Recently a new hypnotic with a mode of action different from other hypnotics has been introduced. Ramelteon is a melatonin receptor agonist with high affinity for melatonin MT1 and MT2 receptors. It is indicated for sleep onset insomnia but it has not been shown to produce a sleep maintenance benefit. It does not affect the GABA-A receptor complex, is not addicting and is not scheduled.

Therefore, it is desirable to have a pharmacological agent for the treatment of insomnia which is more effective and/or has fewer side effects that those currently used.

SUMMARY OF THE INVENTION

In some embodiments, the present invention relates to a method for the treatment of a patient suffering from insomnia including administering to the patient doxepin, a pharmaceutically-acceptable salt or a prodrug thereof in a daily dosage ranging from about 0.0001 to about 499 milligrams, wherein the doxepin, the salt or the prodrug is a geometric isomer mixture containing about 18.2% to about 100.0% of the cis-(Z) isomer or is 100% cis-(Z) isomer. In some embodiments, the present invention relates to a method for the treatment of a patient suffering from sleep maintenance insomnia, characterized by fragmented sleep during the $8^{th}$ hour of sleep, comprising: identifying a patient having a sleep disorder in which, for a given 8 hour period of desired sleep, the patient experiences fragmented sleep during the final 60 minutes of said period; and administering to said patient, prior to the start of the sleep period, a dosage of doxepin or a pharmaceutically-acceptable salt thereof that is effective to improve sleep maintenance insomnia by reducing early awakenings during the $8^{th}$ hour of the sleep period, wherein the dosage ranges from about 0.1 to about 20 milligrams, wherein the doxepin or salt thereof is a geometric isomer mixture containing about 18.2% to about 100.0% of the cis-(Z) isomer or is 100% cis-(Z) isomer. In some embodiments, the resent invention relates to a method for the treatment of a patient suffering from sleep maintenance insomnia characterized by early awakenings during the 8th hour of sleep, comprising: identifying a patient having a sleep disorder in which, for a given 8 hour period of desired sleep, the patient experiences early awakenings during the final 60 minutes of said period; and administering to said patient, prior to the start of the sleep period, a dosage of doxepin or a pharmaceutically-acceptable salt thereof that is effective to improve sleep maintenance insomnia by reducing early awakenings during the 8th hour of the sleep period, wherein the dosage ranges from about 0.1 to about 20 milligrams, wherein the doxepin or salt thereof is a geometric isomer mixture containing about 18.2% to about 100.0% of the cis-(Z) isomer or is 100% cis-(Z) isomer. The geometric isomer mixture may contain more than 20%, 50%, 90%, or 95% of the cis-(Z) isomer. The geometric isomer mixture can, in some embodiments, contain at least 99.5% or 99.9% of the cis-(Z) isomer. Alternatively, the geometric isomer mixture may contain 100.0% of the cis-(Z) isomer. The geometric isomer mixture may contain about 20% to about 99.9% of the cis-(Z) isomer, about 30% to about 99.5% of the cis-(Z)isomer, about 50% to about 99% of the cis-(Z) isomer, about 75% to about 97% of the cis-(Z) isomer, or about 90% to about 94.9% of the cis-(Z) isomer.

In some embodiments, the pharmaceutically-acceptable salt of doxepin can be the hydrochloride salt thereof. In some embodiments, the prodrug of doxepin can be a prodrug ester.

The daily dosage may be about 0.001 to about 249 milligrams, about 0.001 to about 99 milligrams, about 0.001 to about 49 milligrams, 0.001 to about 24 milligrams, about 20 to about 49 milligrams, about 0.01 to about 24 milligrams, about 0.01 to about 20 milligrams, about 0.01 to about 10 milligrams, or about 0.1 to about 5 milligrams.

In some embodiments, the insomnia is a chronic insomnia. In other embodiments, the insomnia is a non-chronic insomnia. The non-chronic insomnia may be a transient or a short-term insomnia. The insomnia may be, for example, onset insomnia or maintenance insomnia.

The patient in some embodiments can be suffering from depression. In other embodiments, the patient is not suffering from depression.

In some embodiments, a method disclosed herein can further include administering at least one of ramelteon, VEC-162, gaboxadol, APD125, tiagabine, trazodone, indiplon, AVE 8488, MDL 100907, AVE 8488, MDL 100907, ketanserin, eszopiclone, zolpidem, or zaleplon. In some aspects, more than one of the foregoing can be administered. In some embodiments, a method disclosed herein can further include administering at least one additional medication. The at least one additional medication may be selected from a 5-HT2 antagonist, a H3 agonist, an orexin antagonist, a noradrenergic antagonist, a galanin agonist, a CRH antagonist, a GABA-A direct agonists, a GABA reuptake inhibitor, tiagabine, a growth hormone, a growth hormone agonist, estrogen, an estrogen agonist, or a melatonin agonist.

In some embodiments, the present invention relates to a composition including a pharmaceutically-acceptable carrier and doxepin, a pharmaceutically-acceptable salt of doxepin, or a prodrug of doxepin in a unit dosage form of about 0.0001 milligrams to about 499 milligrams, wherein the doxepin, the salt or the prodrug is a geometric isomer mixture containing about 18.2% to about 100.0% of the cis-(Z) isomer or is 100% cis-(Z) isomer. The geometric isomer mixture may contain more than 20%, 50%, 90%, or 95% of the cis-(Z) isomer. In some embodiments, the geometric isomer mixture can contain at least 99.5% or 99.9% of the cis-(Z) isomer. In other embodiments, the geometric isomer mixture can contain 100% of the cis-(Z) isomer. The geometric isomer mixture may contain about 20% to about 99.9% of the cis-(Z) isomer, about 30% to about 99.5% of the cis-(Z) isomer, about 50% to about 99% of the cis-(Z) isomer, about 75% to about 97% of the cis-(Z) isomer, or about 90% to about 94.9% of the cis-(Z) isomer.

In some embodiments, the pharmaceutically-acceptable salt of doxepin is the hydrochloride salt thereof. The prodrug may be an ester.

The unit dosage form can be, in some embodiments, about 0.001 to about 249 milligrams, about 0.001 to about 99 milligrams, about 0.001 to about 49 milligrams, about 0.001 to about 24 milligrams, about 0.1 to about 24 milligrams, about 0.1 to about 20 milligrams, about 0.1 to about 10 milligrams, or about 0.1 to about 5 milligrams.

In some embodiments, the composition may be formulated for oral or nasal administration. The unit dosage form can be, for example, a pill, a tablet, a capsule, a gel cap, or a fast melt formulation.

In some embodiments, the present invention relates to a method for treating insomnia including administering to a patient a metabolite of doxepin, a pharmaceutically-acceptable salt thereof, or a prodrug thereof in a daily dosage ranging from about 0.0001 to about 499 milligrams, wherein the metabolite of doxepin, the salt or the prodrug is a geometric isomer mixture containing about 18.2% to about 100.0% of the cis-(Z) isomer or is 100% cis-(Z) isomer. The geometric isomer mixture may contain more than 20%, 50%, 90%, or 95% of the cis-(Z) isomer. In some embodiments, the geometric isomer mixture can contain at least 99.5% or 99.9% of the cis-(Z) isomer. In other embodiments, the geometric isomer mixture can contain 100% of the cis-(Z) isomer. The geometric isomer mixture may contain about 20% to about 99.9% of the cis-(Z) isomer, about 30% to about 99.5% of the cis-(Z) isomer, about 50% to about 99% of the cis-(Z) isomer, about 75% to about 97% of the cis-(Z) isomer, or about 90% to about 94.9% of the cis-(Z) isomer.

The metabolite of doxepin, the pharmaceutically-acceptable salt, or the prodrug may be administered in a dosage ranging from about 0.001 to about 249 milligrams, about 0.001 to about 99 milligrams, about 0.001 to about 49 milligrams, or about 0.01 to about 24 milligrams.

The insomnia may be a chronic or a non-chronic insomnia. The non-chronic insomnia may be a transient or a short-term insomnia. The insomnia can, in some embodiments, be selected from the group consisting of onset insomnia and maintenance insomnia. The metabolite may be desmethyldoxepin, hydroxydoxepin, hydroxyl-N-desmethyldoxepin, or doxepin N-oxide.

A method disclosed herein can, in some embodiments, further can include administering at least one of ramelteon, eszopiclone, zolpidem, or zaleplon. A method disclosed herein, can, in some embodiments, further include administering at least one additional medication. The at least one additional medication may be a sleep medication. The at least one additional sleep medication may be, for example, a 5-HT2 antagonist, a H3 agonist, an orexin antagonist, a noradrenergic antagonist, a galanin agonist, a CRH antagonist, a GABA-A direct agonist, a GABA reuptake inhibitor, a growth hormone, a growth hormone agonist, estrogen, an estrogen agonist, an ion channel blocker, and a melatonin agonist. The 5-HT2 antagonist may be one selected from ketanserin, risperidone, eplivanserin, pruvanserin, MDL 100907, APD125, and AVE 8488. The at least one additional medication may be selected from ketanserin, Gaboxadol, and tiagabine. The ion channel blocker may be one selected from lamotrigine, gabapentin, and pregabalin. The melatonin agonist may be one selected from melatonin, remelteon, and agomelatine. In some embodiments, the at least one additional medication can be selected from clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, zolpidem, gaboxadol, vigabatrin, tiagabine, estazolam and the like.

In some embodiments, the present invention relates to a composition including a pharmaceutically-acceptable carrier and a metabolite of doxepin, a pharmaceutically-acceptable salt of the metabolite, or a prodrug of the metabolite in a unit dosage form of about 0.0001 milligrams to about 499 milligrams, wherein the doxepin, the salt or the prodrug is a geometric isomer mixture containing about 18.2% to about 100.0% of the cis-(Z) isomer of the metabolite. The geometric isomer mixture may contain more than 20%, 50%, 90%, or 95% of the cis-(Z) isomer of the metabolite. In some embodiments, the geometric isomer mixture can contain at least 99.5% or 99.9% of the cis-(Z) isomer of the metabolite. In other embodiments, the geometric isomer mixture can contain 100% of the cis-(Z) isomer of the metabolite. The geometric isomer mixture may contain about 20% to about 99.9% of the cis-(Z) isomer of the metabolite, about 30% to about 99.5% of the cis-(Z) isomer of the metabolite, about 50% to about 99% of the cis-(Z) isomer of the metabolite, about 75% to about 97% of the cis-(Z) isomer of the metabolite, or about 90% to about 94.9% of the cis-(Z) isomer of the metabolite.

The pharmaceutically-acceptable salt of the metabolite may be the hydrochloride salt thereof. The metabolite may be desmethyldoxepin, hydroxydoxepin, hydroxyl-N-desmethyldoxepin, or doxepin N-oxide. The prodrug may be an ester, for example.

The unit dosage may be about 0.001 to about 249 milligrams, about 0.001 to about 99 milligrams, about 0.001 to about 49 milligrams, about 0.001 to about 24 milligrams, about 0.1 to about 24 milligrams, about 0.1 to about 20 milligrams, about 0.1 to about 10 milligrams, or about 0.1 to about 5 milligrams.

The composition may be formulated for oral or nasal administration. The unit dosage form may be selected from the group consisting of a pill, a tablet, a capsule, a gel cap, and a fast melt formulation.

In some embodiments, the present invention relates to a method for the treatment of a patient suffering from insomnia including providing a composition enriched in cis isomer compared to the ratio of the cis-/trans-isomers in doxepin as typically prepared, a metabolite of doxepin, a salt of doxepin, a salt of a metabolite of doxepin, a prodrug of doxepin, or a prodrug of a metabolite of doxepin and administering/prescribing to the patient the enriched composition of cis doxepin, a metabolite of doxepin, a salt of doxepin, a salt of a metabolite of doxepin, a prodrug of doxepin, or a prodrug of a metabolite of doxepin.

In some embodiments, the present invention relates to a composition including doxepin, a metabolite of doxepin, a salt of doxepin, a salt of a metabolite of doxepin, a prodrug of doxepin, or a prodrug of a metabolite of doxepin, wherein the ratio of the cis-/trans-isomers is greater than that found in the doxepin as typically prepared.

In some embodiments, the present invention relates to a method for the treatment of a patient suffering from insomnia including providing a composition enriched in cis isomer compared to the ratio of the cis-/trans-isomers in a metabolite of doxepin, a salt of doxepin, a salt of a metabolite of doxepin, a prodrug of doxepin, or a prodrug of a metabolite of doxepin, comparing the ratio of the cis-/trans-isomers to the ratio of cis-/trans-isomers in doxepin as typically prepared, and administering/prescribing to the patient the enriched composition of the cis isomer of the metabolite of doxepin, salt of doxepin, salt of the metabolite of doxepin, prodrug of doxepin, or prodrug of the metabolite of doxepin.

DETAILED DESCRIPTION OF THE PREFERRED EMBODIMENT

Generally, embodiments of the present invention relate to doxepin isomers, doxepin metabolite isomers, including pharmaceutically acceptable salts and prodrugs of the same, as well as compositions of the same. In some aspects the isomers can be in a substantially pure form (e.g., at least 80%, 85%, 90%, 95%, 97%, 99%, 99.5%, 99.9% or 100% cis isomer). In other aspects the isomers can be in an isomeric mixture as described herein. Also, embodiments relate to the use of the cis-(Z) isomer or geometric isomeric mixtures containing specified ratios of the cis-(Z) to trans-(E) isomers of doxepin or doxepin metabolites, prodrugs, or salts of the same to treat an individual suffering from a sleep disorder, for example a disorder such as insomnia. Several examples of insomnias that can be treated using the isomers and isomeric mixtures are described below. In some embodiments, the sleep disorder, such as insomnia, can be treated by administering low dosages of doxepin or doxepin metabolite isomers and isomeric mixtures, while in others it can be administered in a higher dosage. Various dosages of isomers are described below. Surprisingly, when used in specific isomeric ratios described herein, low doses of doxepin isomers and isomers of doxepin metabolites are very effective in treating insomnia with very minimal side effects. The isomers and isomer mixtures, as well as their uses, as described herein have not been described previously, particularly for use in the treatment of sleep disorders.

Doxepin is a tricyclic compound approved for the treatment of depression and anxiety. The recommended daily dose for the treatment of depression and anxiety ranges from 75 milligrams to 300 milligrams. Doxepin, unlike most FDA approved products for the treatment of insomnia, is not a Schedule IV controlled substance.

U.S. Pat. Nos. 5,502,047 and 6,211,229, the entire contents of which are incorporated herein by reference, describe the use of doxepin for the treatment of chronic and non-chronic (e.g., transient/short term) insomnias at dosages far below those used to treat depression.

No studies have investigated whether sleep disorders can be effectively treated by isomers or geometric isomeric mixtures of doxepin or doxepin metabolites, pharmaceutically-acceptable salts or prodrugs of the same, in particular mixtures containing higher proportions of the cis-(Z) isomer than found in doxepin as typically prepared. According to USP 25, 2002. United States Pharmacopeial Convention, Inc., Rockville, Md. P. 615, doxepin hydrochloride U.S.P. is a geometric isomer mixture "containing not less than 13.6% and not more than 18.1%" of the cis isomer and "not less than 81.4% and not more than 88.2%" of the trans isomer.

Methods of Treating Sleep Disorders

Some embodiments of the instant invention relate to methods for the treatment of a patient suffering from a sleep disorder, such as insomnia. The methods can include the administration to a patient of an isomer of doxepin, a mixture of doxepin isomers, or an isomer of a metabolite of doxepin, a mixture of metabolite isomers, or a pharmaceutically-acceptable salt or a prodrug thereof any of the aforementioned substances. The medication can be administered in any suitable dosage to treat the sleep disorder, including the dosages described herein. For example, the medication can be administered in a daily dosage ranging from about 0.001, to about 9 milligrams, to about 24 milligrams, to about 49 milligrams, to about 99 milligrams, to about 249 milligrams, or to about 499 milligrams. Also, as previously mentioned, the isomers can be administered alone (e.g., in a substantially pure or pure form) or in an isomeric mixture. Examples of isomeric ratios are described elsewhere herein. As an example, the medication can contain about 18.2% to about 100.0%, about 20% to about 100.0%, about 50% to about 100.0%, about 80% to about 100.0%, about 95% to about 100.0%, about 99% to about 100.0%, about 99.5% to about 100.0%, about 99.9% to about 100.0%, or 100.0% of the cis-(Z) isomer. In some aspects a substantially pure isomer can be administered, for example, at least 80%, 85%, 90%, 95%, 97%, 98%, 99%, 99.5%, or 99.9% cis-(Z) isomer. In some aspects a pure or 100% cis-(Z) isomer can be used in the methods. The insomnia can be any insomnia, including those described herein.

Some embodiments relate to methods for the treatment of a patient suffering from insomnia, for example, by providing a composition enriched in cis isomer compared to the ratio of the cis-/trans-isomers in doxepin as typically prepared, a metabolite of doxepin, a salt of doxepin, a salt of a metabolite of doxepin, a prodrug of doxepin, or a prodrug of a metabolite of doxepin; and administering/prescribing to said patient the enriched composition of cis isomer of doxepin, a metabolite of doxepin, a salt of doxepin, a salt of a metabolite of doxepin, a prodrug of doxepin, or a prodrug of a metabolite of doxepin. "Native", "native-occurring" or "as typically prepared" can refer, for example, to a common form of the compound available in the pharmaceutical or chemical industry or a form produced by standard chemical synthesis.

Some embodiments relate to methods for the treatment of a patient suffering from insomnia, for example, by providing a composition enriched in cis isomer compared to the ratio of the cis-/trans-isomers in one or more of the following: a metabolite of doxepin, a salt of doxepin, a salt of a metabolite of doxepin, a prodrug of doxepin, or a prodrug of a metabolite of doxepin; comparing the ratio of the cis-/trans-isomers to the ratio of cis-/trans-isomers in doxepin as typically prepared; and administering/prescribing to the patient the enriched composition of the cis isomer of the metabolite of doxepin, salt of doxepin, salt of the metabolite of doxepin, prodrug of doxepin, or prodrug of the metabolite of doxepin.

Also, some embodiments relate to compositions that include doxepin, a metabolite of doxepin, a salt of doxepin, a salt of a metabolite of doxepin, a prodrug of doxepin, or a prodrug of a metabolite of doxepin, wherein the ratio of the cis-/trans-isomers in the composition is greater than that found in the compound as typically synthesized.

As mentioned above and elsewhere, the methods described herein can be used to treat individuals suffering from a sleep disorder, such as insomnia. The term "insomnia" generally refers to sleep problems characterized by difficulty falling asleep, wakings during the night, or waking up earlier than desired. Examples of insomnia include chronic and non-chronic insomnias.

For chronic (e.g., greater than 3-4 weeks) or non-chronic insomnias, a patient may suffer from difficulties in sleep onset, sleep maintenance (interruption of sleep during the night by periods of wakefulness), sleep duration, sleep efficiency, premature early-morning awakening, or a combination thereof. Also, the insomnia may be attributable to the concurrent use of other medication. The non-chronic insomnia can be, for example, a short term insomnia or a transient insomnia. The chronic or non-chronic insomnia can be a primary insomnia or an insomnia that is secondary or attributable to another condition, for example a disorder such as depression or chronic fatigue syndrome. In some aspects, the patient can be one who is not suffering from an insomnia that is a component of a disease, the patient can be one whose insomnia is unrelated to a disease, or a patient can be treated who is otherwise healthy, for example. As previously mentioned, the chronic or non-chronic insomnia can be a primary insomnia, that is, one that is not attributable to another disorder such as a mental or neurological disorder, a general medical condition, or a substance. In many cases, such conditions may be associated with a chronic insomnia and can include, but are not limited to, insomnia attributable to a diagnosable DSM-IV disorder, a disorder such as anxiety or depression, or a disturbance of the physiological sleep-wake system. In some aspects the insomnia can be non-chronic, or of short duration (e.g., less than 3-4 weeks). Examples of causes of such insomnia may be extrinsic or intrinsic and include, but are not limited to environmental sleep disorders as defined by the International Classification of Sleep Disorders (ICSD) such as inadequate sleep hygiene, altitude insomnia or adjustment sleep disorder (e.g., bereavement). Also, short-term insomnia may also be caused by disturbances such as shift-work sleep disorder.

Also, some embodiments can include the use of an isomer of doxepin, a mixture of doxepin isomers, an isomer of a metabolite of doxepin, a mixture of metabolite isomers, or a pharmaceutically-acceptable salt or a prodrug of any of the aforementioned substances in combination with other insomnia or sleep medications. For example, the methods can include the use of one or more of ramelteon, VEC-162, APD125, trazodone, AVE 8488, MDL 100907, or the like. Further, the methods can include the use of one or more of 5-HT2 antagonists (such as ketanserin), H3 agonists, orexin antagonists, noradrenergic antagonists, galanin agonists and CRH antagonists. Similarly, the methods can use GABA modulators (e.g., compounds that facilitate GABA neurotransmission) such as benzodiazepines, nonbenzodiazepine positive modulators such as eszopiclone, indiplon, zolpidem and zaleplon, GABA-A direct agonists (such as gaboxadol), and GABA reuptake inhibitors (such as tiagabine). Finally, the methods can use growth hormone and growth hormone agonists, estrogen and estrogen agonists, melatonin agonists or the like. The methods can also include the use of one or more antihistamines.

An isomer of doxepin, a mixture of doxepin isomers, an isomer of a metabolite of doxepin, a mixture of metabolite isomers, or a pharmaceutically-acceptable salt or a prodrug of any of the aforementioned substances may be used in combination with ramelteon. Ramelteon ((S)—N-[2-(1,6,7,8-tetrahydro-2H-indeno-[5,4-b]furan-8-yl)ethyl]propionamide) can be used in any dosage, but preferably can be used in a dosage of about 0.5 milligrams to about 20 milligrams. More preferably, about 4, 8 or 16 milligrams can be used, for example.

An isomer of doxepin, a mixture of doxepin isomers, an isomer of a metabolite of doxepin, a mixture of metabolite isomers, or a pharmaceutically-acceptable salt or a prodrug of any of the aforementioned substances may be used in combination with eszopiclone. Eszopiclone also can be used in any suitable dosage. For example, the dosage can be about 0.1 to about 10 milligrams. Preferably, as an example, the dosage can be about 1, 2, or 3 milligrams.

An isomer of doxepin, a mixture of doxepin isomers, an isomer of a metabolite of doxepin, a mixture of metabolite isomers, or a pharmaceutically-acceptable salt or a prodrug of any of the aforementioned substances may be used in combination with zolpidem. Zolpidem (N,N,6-trimethyl-2-p-tolylimidazo[1,2-a] pyridine-3-acetamide L-(+)-tartrate (2:1)) also can be used in any suitable dosage. For example, the dosage can be about 0.1 to about 20 milligrams. In some embodiments, as an example, the dosage can be about 6.25-milligrams, 12.5 milligrams or a dosage that is a factor thereof. In other embodiments, the dosage can be about 5-milligrams, 10-milligrams or a dosage that is a factor thereof.

Furthermore, an isomer of doxepin, a mixture of doxepin isomers, an isomer of a metabolite of doxepin, a mixture of metabolite isomers, or a pharmaceutically-acceptable salt or a prodrug of any of the aforementioned substances may be used in combination with zaleplon. Zaleplon (N-[3-(3-cyantopryazolo[1,5-a]pyrimidin-7-yl)phenyl]-N-ethylacetamide) can be used in any suitable dosage. For example, the dosage can be about 0.1 to about 20 milligrams. Preferably, as an example, the dosage can be about 5, 10 or 20 milligrams, for example.

An isomer of doxepin, a mixture of doxepin isomers, an isomer of a metabolite of doxepin, a mixture of metabolite isomers, or a pharmaceutically-acceptable salt or a prodrug of any of the aforementioned substances may be used in combination with gaboxadol. Gaboxadol (7-tetra hydroisoxazolo[5,4-c]pyridin-3-ol) can be used in any suitable dosage. For example, the dosage can be about 0.1 to about 20 40 milligrams. Preferably, as an example, the dosage can be about 0.5 to about 20 milligrams or 10 or 15 milligrams, for example.

An isomer of doxepin, a mixture of doxepin isomers, an isomer of a metabolite of doxepin, a mixture of metabolite isomers, or a pharmaceutically-acceptable salt or a prodrug of any of the aforementioned substances may be used in combination with VEC-162. VEC-162 can be used in any suitable dosage. For example, the dosage can be about 0.1 to about 100 milligrams. Preferably, as an example, the dosage can be about 10, 20, 50 or 100 milligrams, for example.

An isomer of doxepin, a mixture of doxepin isomers, an isomer of a metabolite of doxepin, a mixture of metabolite isomers, or a pharmaceutically-acceptable salt or a prodrug of any of the aforementioned substances may be used in combination with indiplon. Indiplon (N-methyl-N-[3-[3-(2-thienylcarbonyl)-pyrazolo[1,5-α]pyrimidin-7-yl]phenyl]acetamide) can be used in any suitable dosage. For example, the dosage can be about 0.1 to about 10 milligrams. Preferably, as an example, the dosage can be about 5 or 10 milligrams, for example.

An isomer of doxepin, a mixture of doxepin isomers, an isomer of a metabolite of doxepin, a mixture of metabolite isomers, or a pharmaceutically-acceptable salt or a prodrug of any of the aforementioned substances may be used in combination with MDL 100907. MDL 100907 (Sanofi-Aventis) can be used in any suitable dosage. For example, the dosage can be about 0.5 to about 100 milligrams, preferably from about 1 to about 50 milligrams.

An isomer of doxepin, a mixture of doxepin isomers, an isomer of a metabolite of doxepin, a mixture of metabolite isomers, or a pharmaceutically-acceptable salt or a prodrug of any of the aforementioned substances may be used in combination with APD125. APD125 (Arena Pharmaceuticals) can be used in any suitable dosage. For example, the dosage can be about 1 to about 160 milligrams, preferably about 5 to about 80 milligrams, or more preferably about 10 to about 40 milligrams.

An isomer of doxepin, a mixture of doxepin isomers, an isomer of a metabolite of doxepin, a mixture of metabolite isomers, or a pharmaceutically-acceptable salt or a prodrug of any of the aforementioned substances may be used in combination with AVE8488. AVE 8488 (Sanofi-Aventis) can be used in any suitable dosage. For example, the dosage can be about 0.5 to about 100 milligrams, preferably from about 1 to about 50 milligrams.

It should be noted that in some aspects, the methods can specifically exclude one or more of any of the sleep disorders described in the previous paragraph or elsewhere herein. For example, without being limited thereto, in some aspects the methods can specifically exclude treating a chronic insomnia. As another example, without being limited thereto, in some aspects the methods can specifically exclude treating an insomnia that is attributable to a condition such as depression, anxiety or chronic fatigue. As a further example, in some aspects the methods and compositions can specifically exclude one or more of the combination drugs.

Compounds of Doxepin and Metabolites

Doxepin:

Doxepin has the following structure:

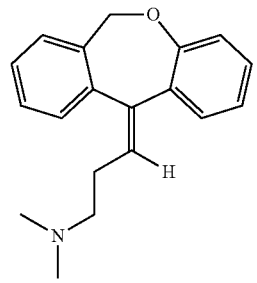 [SMILES: CN(C)CC/C=C1\c2ccccc2COc2ccccc21]

For all compounds disclosed herein, unless otherwise indicated, where a carbon-carbon double bond is depicted, both the cis and trans stereoisomers, as well as mixtures thereof are encompassed.

It is contemplated that doxepin for use in the methods described herein can be obtained from any suitable source or made by any suitable method. As mentioned, doxepin is approved and available in higher doses (75-300 milligrams) for the treatment of depression and anxiety. Doxepin HCl is available commercially and may be obtained in capsule form from a number of sources. Doxepin is marketed under the commercial name SINEQUAN® and in generic form, and can be obtained in the United States generally from pharmacies in capsule form in amounts of 10, 25, 50, 75, 100 and 150 mg dosage, and in liquid concentrate form at 10 mg/mL. Doxepin HCl can be obtained from Plantex Ltd. Chemical Industries (Hakadar Street, Industrial Zone, P.O. Box 160, Netanya 42101, Israel), Sifavitor S.p.A. (Via Livelli 1—Frazione, Mairano, Italy), or from Dipharma S.p.A. (20021 Baranzate di Bollate, Milano, Italy). Also, doxepin is commercially available from PharmacyRx (NZ) (2820 $1^{st}$ Avenue, Castlegar, B.C., Canada) in capsule form in amounts of 10, 25, 50, 75, 100 and 150 mg. Furthermore, Doxepin HCl is available in capsule form in amounts of 10, 25, 50, 75, 100 and 150 mg and in a 10 mg/ml liquid concentrate from CVS Online Pharmacy Store (CVS.com).

Furthermore, doxepin (11-(3-dimethylaminopropylidene)-6,11-dihydrodibenzo(b,e)oxepin) can be prepared according to the method taught in U.S. Pat. No. 3,438,981, which is incorporated herein by reference in its entirety. An example preparation is described below in Example 1.

One available form of doxepin is a mixture of cis-(Z) and trans-(E) isomers in a ratio of approximately 15 to 85, respectively, as shown below. (Wyatt et al., Applied Spectroscopy. (1986) 40:369-373; which is incorporated herein by reference in its entirety). (E)-doxepin and (Z)-doxepin have the following structures:

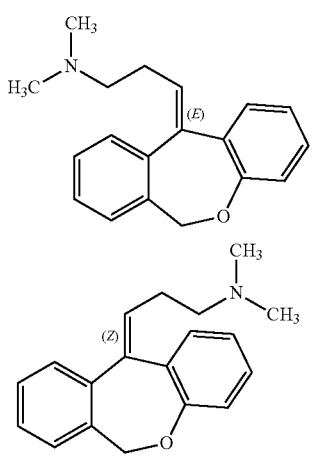

The doxepin isomers can be prepared by any suitable method. For example, doxepin can be prepared in either of its (Z) or (E) isomers from 11-[3-(Dimethylamino)propyl]-6,11-dihydrodibenzo[b,e]oxepin-11-ol as taught in U.S. Pat. No. 3,420,851, which is incorporated herein by reference in its entirety. Further, the (Z) or (E) isomers can be isolated via crystallization of doxepin hydrochloride from a mixture of ethanol and diethyl ether as taught in the incorporated material of U.S. Pat. No. 3,420,851. For example, preferably the ratio of Z/E isomers can be about 18.2/81.8, about 20/80, about 30/70, about 50/50, about 75/25, about 80/20, about 90/10, about 95/5, or about 99/1. In some aspects, the ratio of Z/E isomers can vary from about 18.2/81.8 to about 100/0, from about 20/80 to about 99.9/0.1, from about 30/70 to about 99.5/0.5, from about 50/50 to about 99/1, from about 75/25 to about 97/3, from about 80/20 to about 94.9/5.1, or the like. In some embodiments, a substantially pure or pure the cis isomer can be prepared. As used herein, the cis isomer can refer to a mixture containing at least 80%, at least 85%, at least 90%, at least 95%, at least 98%, at least 99%, at least 99.5%, at least 99.9%, or 100% of the cis isomer.

Each of the references discussed above is incorporated by reference in its entirety. In some aspects, the teachings of one or more of the references can be included or combined with instant methods or embodiments, while in other aspects the teachings of one or more of the references can be specifically excluded from the methods and embodiments described herein. As one example, the dosages used or the patient population that is treated (e.g., age, health/disease profile, etc.) in a reference can be excluded or included from the methods and embodiments described herein.

Metabolites of Doxepin:

Also, isomers of doxepin metabolites can be prepared and used. By way of illustration, some examples of metabolites of doxepin can include, but are not limited to, desmethyldoxepin, hydroxydoxepin, hydroxyl-N-desmethyldoxepin, doxepin N-oxide, N-acetyl-N-desmethyldoxepin, N-desmethyl-N-formyldoxepin, quaternary ammonium-linked glucuronide, 2-O-glucuronyldoxepin, didesmethyldoxepin, 3-O-glucuronyldoxepin, or N-acetyldidesmethyldoxepin. The metabolites of doxepin can be obtained or made by any suitable method, including the methods described above for doxepin.

Desmethyldoxepin has the following structure:

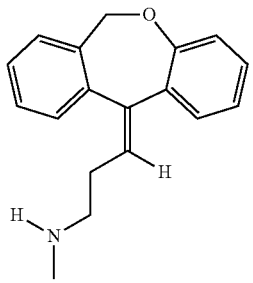 [SMILES: CNCC/C=C1\c2ccccc2COc2ccccc21]

Desmethyldoxepin is commercially available as a forensic standard. For example, it can be obtained from Cambridge Isotope Laboratories, Inc. (50 Frontage Road, Andover, Mass. Desmethyldoxepin for use in the methods discussed herein can be prepared by any suitable procedure. For example, desmethyldoxepin can be prepared from 3-methylaminopropyl triphenylphosphonium bromide hydrobromide and 6,11-dihydrodibenz(b,e)oxepin-11-one according to the method taught in U.S. Pat. No. 3,509,175, which is incorporated herein by reference in its entirety. As another example, desmethyldoxepin can be prepared in its (E) and (Z) isomers from desmethyldoxepin hydrochloride as taught in U.S. Pat. No. 5,332,661, which is incorporated herein by reference in its entirety.

Hydroxydoxepin has the following structure:

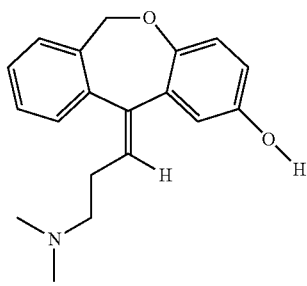 [SMILES: CN(C)CC/C=C1\c2ccccc2COc2ccc(O)cc21]

2-Hydroxydoxepin can be prepared in its (Z) and (E) isomers as taught by Shu et al. (Drug Metabolism and Disposition (1990) 18:735-741), which is incorporated herein by reference in its entirety.

Hydroxyl-N-desmethyldoxepin has the following structure:

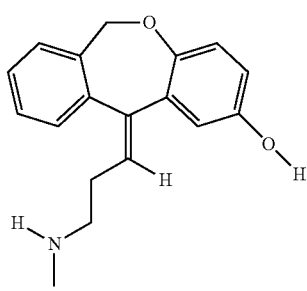 [SMILES: CNCC/C=C1\c2ccccc2COc2ccc(O)cc21]

2-Hydroxy-N-desmethyldoxepin can be prepared in its (Z) and (E) isomers as described in Examples 8-9.

Doxepin N-oxide has the following structure:

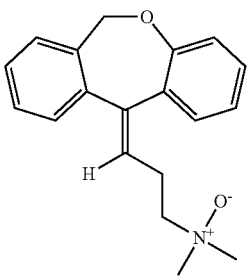 [SMILES: C[N+](C)([O-])CC/C=C1/c2ccccc2COc2ccccc21]

Doxepin-N-oxide may be prepared by any suitable method. For example, doxepin-N-oxide can be prepared as taught by Hobbs (*Biochem Pharmacol* (1969) 18:1941-1954), which is hereby incorporated by reference in its entirety.

The (Z) and (E) isomers of doxepin-N-oxide can be prepared by any suitable method. For example, the N-oxide form of the (Z) isomer of doxepin can be prepared as described above for doxepin, by using purified (Z)-doxepin as a starting material. Likewise, N-oxide form of the (E) isomer of doxepin can be prepared as described above for doxepin, by using purified (E)-doxepin as a starting material.

N-acetyl-N-desmethyldoxepin has the following structure:

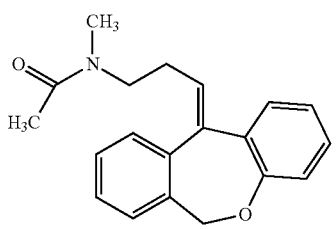 [SMILES: CC(=O)N(C)CC/C=C1\c2ccccc2COc2ccccc21]

The (Z) and (E) isomers of N-acetyl-N-desmethyldoxepin can be prepared by any suitable means. For example, (E)-N-acetyl-N-desmethyldoxepin has been produced in filamentous fungus incubated with doxepin as taught by Moody et al. (*Drug Metabolism and Disposition* (1999) 27:1157-1164), hereby incorporated by reference in its entirety.

N-desmethyl-N-formyldoxepin has the following structure:

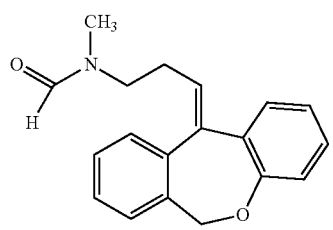 [SMILES: CN(C=O)CC/C=C1\c2ccccc2COc2ccccc21]

The (Z) and (E) isomers of N-desmethyl-N-formyldoxepin may be prepared by any suitable means. For example, (E)-N-desmethyl-N-formyldoxepin has been produced in filamentous fungus incubated with doxepin as taught by Moody et al. (*Drug Metabolism and Disposition* (1999) 27:1157-1164), hereby incorporated by reference in its entirety.

N-acetyldidesmethyldoxepin has the following structure:

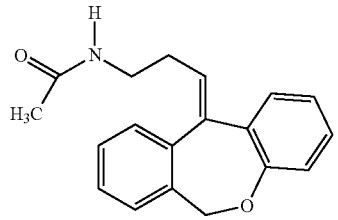 [SMILES: CC(=O)NCC/C=C1\c2ccccc2COc2ccccc21]

The (Z) and (E) isomers of N-acetyldidesmethyldoxepin may be prepared by any suitable means. For example, (E)-N-acetyldidesmethyldoxepin has been produced in filamentous fungus incubated with doxepin as taught by Moody et al. (*Drug Metabolism and Disposition* (1999) 27:1157-1164), hereby incorporated by reference in its entirety.

Didesmethyldoxepin has the following structure:

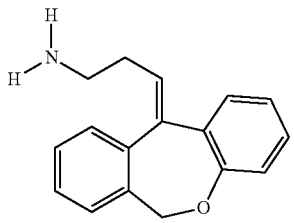 [SMILES: NCC/C=C1\c2ccccc2COc2ccccc21]

The (Z) and (E) isomers of didesmethyldoxepin can be prepared by any suitable means. For example, (Z)- and (E)-didesmethyldoxepin have been isolated from plasma and cerebrospinal fluid of depressed patients taking doxepin, as taught by Deuschle et al. (*Psychopharmacology* (1997) 131:19-22), hereby incorporated by reference in its entirety.

3-O-glucuronyldoxepin has the following structure:

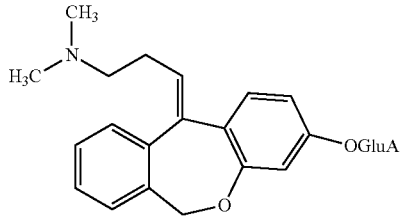

The (Z) and (E) isomers of 3-O-glucuronyldoxepin can be prepared by any suitable means. For example, (E)-3-O-glucuronyldoxepin has been isolated from the bile of rats given doxepin, as described by Shu et al. (*Drug Metabolism and Disposition* (1990) 18:1096-1099), hereby incorporated by reference in its entirety.

2-O-glucuronyldoxepin has the following structure:

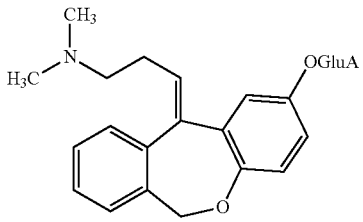

The (Z) and (E) isomers of 2-O-glucuronyldoxepin can be prepared by any suitable means. For example, (E)-2-O-glucuronyldoxepin has been isolated from the bile of rats given doxepin, and also in the urine of humans given doxepin, as described by Shu et al. (Drug Metabolism and Disposition (1990) 18:1096-1099), hereby incorporated by reference in its entirety.

Quaternary ammonium-linked glucuronide of doxepin (doxepin N+-glucuronide) has the following structure:

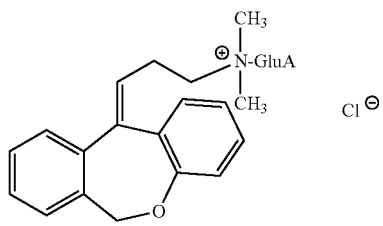

The (Z) and (E) isomers of doxepin N+-glucuronide can be obtained by any suitable means. For example, doxepin N+-glucuronide can be prepared, and the (Z) and (E) isomers thereof can be isolated as taught by Luo et al. (Drug Metabolism and Disposition, (1991) 19:722-724), hereby incorporated by reference in its entirety.

Preferably the ratio of Z/E metabolite isomers can be about 18.2/81.8, about 20/80, about 30/70, about 50/50, about 75/25, about 80/20, about 90/10, about 95/5, about 98/2, about 99/1, about 99.5/0.5, about 99.9/0.1, or about 100/0. In some aspects, the ratio of Z/E isomers can vary from about 18.2/81.8 to about 100/0, from about 20/80 to about 99.9/0.1, from about 30/70 to about 99.5/0.5, from about 50/50 to about 99/1, from about 75/25 to about 97/3, from about 80/20 to about 94.9/5.1, or the like. Preferably, the cis isomer of the metabolite is prepared, wherein the Z/E isomeric ratio is at least 80/20, at least 85/15, at least 90/10, at least 95/5, at least 98/2, at least 99/1, at least 99.5/0.5, at least 99.9/0.1, or is about 100/0.

Pharmaceutically Acceptable Salts and Prodrugs:

As mentioned above, the methods and other embodiments described herein can utilize any suitable pharmaceutically-acceptable salt or prodrug of doxepin or a metabolite of doxepin. Therefore, substitution of salts and prodrugs is specifically contemplated in the various embodiments, even though, only doxepin or doxepin metabolites may be specifically mentioned. The pharmaceutically-acceptable salts and prodrugs can be made by any suitable method. The acids that may be used to prepare pharmaceutically acceptable acid addition salts are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, dislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts.

The term "prodrug" refers to a chemical entity that is rapidly transformed in vivo to yield an active drug, such as for example doxepin or a metabolite of doxepin, for example, by hydrolysis in blood or inside tissues. Examples of pro-drug groups can be found in, for example, T. Higuchi and V. Stella, in "Pro-drugs as Novel Delivery Systems," Vol. 14, A.C.S. Symposium Series, American Chemical Society (1975); H. Bundgaard, "Design of Prodrugs," Elsevier Science, 1985; and "Bioreversible Carriers in Drug Design: Theory and Application," edited by E. B. Roche, Pergamon Press: New York, 14-21 (1987), each of which is hereby incorporated by reference in its entirety.

Preparation and Administration of Pharmaceutical Compositions

As discussed above, the cis-(Z) isomer or specified ratios of the cis-(Z) and trans-(E) isomers of doxepin, of doxepin metabolites, of prodrugs of the same, of salts of the same, and compositions that include cis-(Z) isomer or specified ratios of the cis-(Z) and trans-(E) isomers of doxepin, of a metabolite of doxepin, of a prodrug or of a doxepin salt can be used to treat a sleep disorder, for example, insomnia in a mammal, including a human. Also, doxepin isomer, metabolite isomer or isomer mix, pharmaceutically acceptable salts, and/or prodrugs of the same can be administered alone or in combination with other substances, such as for example, other insomnia or sleep medications, or with other medications that treat a primary illness. For example, doxepin, doxepin metabolite, isomers, prodrugs or salts of the same can be used or administered with ramelteon, VEC-162, gaboxadol, APD125, trazodone, tiagabine, indiplon, AVE 8488, MDL 100907, AVE 8488, MDL 100907, eszopiclone, zolpidem tartrate, zaleplon or the like. Further, doxepin, doxepin metabolite, isomers, prodrugs or salts of the same can be administered with one or more of 5-HT2 antagonists (such as ketanserin), H3 agonists, orexin antagonists, noradrenergic antagonists, galanin agonists, CRH antagonists, GABA-A direct agonists, GABA reuptake inhibitors, growth hormone and growth hormone agonists, estrogen and estrogen agonists, melatonin agonists or the like.

The compositions as described herein can include doxepin, a doxepin isomer or isomers, a metabolite of doxepin, an isomer or isomers of a metabolite of doxepin, a pharmaceutically-acceptable salt of any of the aforementioned (alone or in combination, including with other medications), or a prodrug of any of the aforementioned in a unit dosage form. Unit dosage form can refer to a product form in which premeasured dosages of the drug are packaged, in contrast to bulk preparations. Examples of unit dosage forms are described herein, but several non limiting examples, include, a pill, a tablet, a capsule, a gel cap, a small liquid drug, an ampoule, a fast melt formulation, and the like. The isomers, salts and prodrugs alone or in combination can be included and administered as a composition. Methods of use can include the step of administering a therapeutically-effective amount of the compound or composition to a mammal in need thereof by any suitable route or method of delivery, including those described herein.

Actual dosage levels of the compounds in the pharmaceutical compositions may be varied so as to administer an amount of the compound that is effective to achieve the desired therapeutic response for a particular patient. Examples of dosages that can be used are described more fully elsewhere herein.

Suitable routes of administration include oral, buccal, sublingual, transdermal, rectal, topical, transmucosal, or intestinal administration; parenteral delivery, including intramuscular, subcutaneous, intravenous, intramedullary injections, as well as intrathecal, direct intraventricular, intraperitoneal, intranasal, or intraocular injections.

For oral administration, the compounds can be formulated as pills, tablets, powders, granules, dragees, capsules, liquids, sprays, gels, syrups, slurries, suspensions and the like, in bulk or unit dosage forms, for oral ingestion by a patient to be treated. the compounds can be formulated readily, for example, by combining the active compound with any suitable pharmaceutically acceptable carrier or excipient.

Pharmaceutical preparations for oral use can be obtained by mixing one or more solid excipients with a pharmaceutical composition as described herein, optionally grinding the resulting mixture, and processing the mixture of granules, after adding suitable auxiliaries, if desired, to obtain tablets or dragee cores. Suitable excipients are listed below. Some examples include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

The formulation can be in form suitable for bolus administration, for example. Oral administration can be accomplished using fast-melt formulations, for example. As a further example, the formulations can be included in pre-measured ampules or syringes, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take any suitable form, for example, tablets or lozenges.

For topical administration, the compounds may be formulated for administration to the epidermis as ointments, gels, creams, pastes, salves, gels, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated can be used in the formulation.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly-concentrated solutions.

In addition, any of the compounds and compositions described herein can also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Furthermore, any of the compounds and compositions described herein also can be formulated as a fast-melt preparation. The compounds and compositions can also be formulated and administered as a drip, a suppository, a salve, an ointment, an absorbable material such a transdermal patch, or the like.

One can also administer the compounds of the invention in sustained-release forms or from sustained-release drug delivery systems. A description of representative sustained release materials can be found in the incorporated materials in *Remington: The Science and Practice of Pharmacy* ($20^{th}$ ed, Lippincott Williams & Wilkens Publishers (2003)), which is incorporated herein by reference in its entirety.

A variety of techniques for formulation and administration can be found in *Remington: The Science and Practice of Pharmacy* ($20^{th}$ ed, Lippincott Williams & Wilkens Publishers (2003)), which is incorporated herein by reference in its entirety.

As mentioned above, the compositions and formulations disclosed herein also can include one or more pharmaceutically-acceptable carrier materials or excipients. Such compositions can be prepared for storage and for subsequent administration. Any acceptable carriers or diluents for therapeutic use can be used, including those described, for example, in the incorporated material of *Remington: The Science and Practice of Pharmacy* (2003). The term "carrier" material or "excipient" herein can mean any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, maize starch or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, saline, dextrose, mannitol, lactose, lecithin, albumin, sodium glutamate, cysteine hydrochloride, and the like. Examples of suitable excipients for soft gelatin capsules include vegetable oils, waxes, fats, semisolid and liquid polyols. Suitable excipients for the preparation of solutions and syrups include, without limitation, water, polyols, sucrose, invert sugar and glucose. Suitable excipients for injectable solutions include, without limitation, water, alcohols, polyols, glycerol, and vegetable oils. The pharmaceutical compositions can additionally include preservatives, solubilizers, stabilizers, wetting agents, emulsifiers, sweeteners, colorants, flavorings, buffers, coating agents, or antioxidants. Sterile compositions for injection can be formulated according to conventional pharmaceutical practice as described in the incorporated material in *Remington: The Science and Practice of Pharmacy* (2003). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice. The compound can also be made in microencapsulated form. In addition, if desired, the injectable pharmaceutical compositions may contain minor amounts of nontoxic auxiliary substances, such as wetting agents, pH buffering agents, and the like. If desired, absorption enhancing preparations (for example, liposomes), can be utilized.

The compositions and formulations can include any other agents that provide improved transfer, delivery, tolerance, and the like. These compositions and formulations can include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that at least one active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2):210-8 (2000), Charman W N "Lipids, lipophilic drugs, and oral drug delivery-some emerging concepts." *J Pharm Sci.* 89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

Dosages

The selected dosage level can depend upon, for example, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. Also, a patient can be administered a higher low dose (e.g., 6 milligrams) of the isomer or isomeric mixture, then the drug dosage can be tapered to a lower dosage. It will be understood, however, that the specific dose level for any particular patient can depend upon a variety of factors including the genetic makeup, body weight, general health, diet, time and route of administration, combination with other drugs and the severity of the particular condition being treated.

Any suitable dosage of the cis-(Z) isomer or specified ratios of the cis-(Z) and trans-(E) isomers of doxepin, a metabolite of doxepin, a pharmaceutical salt, or prodrug can be used to treat the sleep disorder such as insomnia. In some aspects, daily dosages of the cis-(Z) isomer or specified ratios of the cis-(Z) and trans-(E) isomers doxepin, of a doxepin metabolite, of a pharmaceutically-acceptable salt of doxepin, or of a prodrug of doxepin may vary from about 0.001 to about 9 milligrams, about 0.001 to about 24 milligrams, about 0.001 to about 49 milligrams, about 0.001 to about 99 milligrams, about 0.001 to about 249 milligrams, about 0.0001 to about 499 milligrams, about 0.01 to about 49 milligrams, about 0.01 to about 40 milligrams, from about 0.1 to about 40 milligrams, about 0.01 to about 24 milligrams, about 0.01 to about 20 milligrams, from about 0.5 to about 30 milligrams, about 1 to about 20 milligrams, or from about 5, 10 or 20 milligrams to about 49 milligrams. Preferably, daily dosages of about 5, about 9, about 24, about 49 milligrams, about 99, about 249, or about 499 or less can utilized. In other aspects, a daily dosage of greater than about 5, about 10, about 20 or about 30 milligrams can be used. However, as it is recognized that each individual may react differently to a given dose of the medication used, the dosages recited should be accorded flexibility. Further, any suitable unit dosage form can be formulated to contain the cis-(Z) isomer or specified ratios of the cis-(Z) and trans-(E) isomers of doxepin, of a doxepin metabolite, of a prodrug of doxepin or of pharmaceutically-acceptable salts of doxepin in the above-recited amounts (e.g., 0.01-49 mg, or higher).

In general, lower doses of the cis-(Z) isomer or specified ratios of the cis-(Z) and trans-(E) isomers of doxepin, of the metabolites, of the salts or of prodrugs of the same can be preferred. These low doses are surprisingly effective and, in most patients, have almost no side effects. In some embodiments, daily dosages can be about 0.01, 0.02, 0.03, 0.04, 0.05, 0.06, 0.07, 0.08 or 0.09 milligrams. In some embodiments about 0.1, 0.2, 0.3, 0.4, 0.5, 0.6, 0.7, 0.8, 0.9, or 1.0 milligrams can be used. In another embodiment, daily dosages of can be about 0.01, 0.5, 1, 2, 3, 4, 5, 6, 7, 8, 9, or 10 milligrams. In another embodiment, daily dosages can be about 11, 12, 13, 14, 15, 16, 17, 18, 19, or 20 milligrams. Therapy at each of the doses described in this paragraph as well as ranges between these doses, are particularly contemplated. These relatively low doses between 0.01 milligrams up to, for example, 2, 3, 4, 5, 10, 15 or 20 milligrams, have reduced side effects and are surprisingly effective.

Further, in some embodiments, daily dosages of the cis-(Z) isomer or of specified ratios of the cis-(Z) and trans-(E) isomers of doxepin may be up to about 25 or 30 milligrams. In another embodiment, daily dosages of the cis-(Z) isomer or of specified ratios of the cis-(Z) and trans-(E) isomers of doxepin may be up to about 35 or 40 milligrams. In another embodiment, daily dosages of the cis-(Z) isomer or of specified ratios of the cis-(Z) and trans-(E) isomers of doxepin may be up to about 45 or 49 milligrams.

Doses of the cis-(Z) isomer or of the specified ratios of the cis-(Z) and trans-(E) isomers of doxepin, of doxepin metabolites, of doxepin salts and of prodrugs of doxepin, for example, greater than 50 milligrams per day can be used. For example a dosage of about 50 milligrams to about 500 milligrams can be used. Also, a dosage of about 50 to about 300, about 50 to about 150, or about 50 to about 75 milligrams can be used, for example. Such doses can treat insomnia in patients not suffering from depression or in otherwise healthy patients.

EXAMPLES

Example 1

Doxepin is prepared by the following method.

(a) A Grignard compound is prepared in the conventional manner from 4.8 g (0.2 gram-atom) magnesium in 100 ml ether and 30 g (34 ml) (3-chloropropyl)-tertbutylether and 16.40 grams (0.078 mol) 6,11-dihydrodibenzo-[b,e]-oxepine-11-one dissolved in 100 ml ether is added in dropwise fashion so that the contents of the flask boil lightly. The mixture is heated for 1 hour with agitation in a reflux condenser to complete the reaction and then it is decomposed with ammonium chloride solution. The product which is obtained by separating, drying and eliminating the solvent produced, when the ether residue (24.0 g) is extracted with ligroin, amounts to 20.3 g (80.0% of theory) of 11-(3-tertbutoxypropyl)-11-hydroxy-6,11-dihydrodibenzo-[b,e]-oxepine, having a melting point of 124-126° C. The (3-chloropropyl)-tertbutyl ether is thereafter obtained in the following manner: 19 g (0.2 mol) 1-chloropropanol-(3), 50 ml liquid isobutylene and 0.5 ml concentrated sulfuric acid are permitted to stand for 24 hours in an autoclave, then are poured into excess sodium bicarbonate solution and extracted with ether. The ether solution is dried with calcium chloride and distilled. 23.6 grams of (3-chloropropyl)-tert-butylether having a boiling point of 150-156° C. (78% of theory) are recovered.

(b) 30.8 grams of the 11-(3-tertbutoxypropyl)-11-hydroxy-6,11-dihydrodibenzo-[b,e]-oxepine obtained according to (a) above and 150 ml absolute alcoholic hydrochloric acid are heated for 1 hour at ebullition. After removing the solvent by evaporation, the residue is crystallized with ligroin, 21.0 grams (88.5% of theory) of 11-(3-hydroxypropylidene)-6,11-dihydrodibenzo-[b,e]-oxepine having a melting point of 108-111° C. were obtained. After recrystallization from acetic acid ester, the compound melts at 112-114° C.

(c) 5.0 ml thionyl chloride dissolved in 5 ml benzene is added dropwise at room temperature to 12.6 g (0.05 mol) of the 11-(3-hydroxypropylidene)-6,11-dihydrodibenzo-[b,e]-oxepine obtained in part (b) above. After 1 hour of standing, the contents of the flask are heated at ebullition for 2 hours. The volatile components are thereafter removed and the remainder distilled using high vacuum. The yield amounts to 10.6 g (78.5% of theory) of 11-(3-chloropropylidene)-6,11-dihydrodibenzo-[b,e]-oxepine having a B.P.0.1 169-172° C., a melting point of 106-111° C. After recrystallization from 20 ml of acetic acid ester, 9.1 g (67.5% of theory) of pure product having a melting point of 113-115° C. is obtained. The crude product can however be used quite easily for further processing.

(d) 5.4 g (0.02 mol) of the 11-(3-chloropropylidene)-6,11-dihydrodibenzo-[b,e]-oxepine, prepared according to (c) above, in 20 ml tetrahydrofuran and 5.5 g (0.12 mol) dimethylamine in 20 ml ethanol is heated together for 3 hours using a glass autoclave and a temperature of 95-100° C. (boiling water bath). Water and 6 N hydrochloric acid are added to the contents of the autoclave and the mixture is extracted with ether. The separated, aqueous-acid components are then made alkaline with dilute caustic soda solution, and the oil thereby separated is taken up in ether. The ether residue, after distillation in a high vacuum, produces 4.1 g (73.5% of theory) of 11-(3-dimethylamino-propylidene)-6,11-dihydrodibenzo-[b,e]-oxepine, having a B.P.$_{0.1}$ 147-150° C. The melting point of the hydrochloride is 182-184° C. (recrystallized from isopropanol).

Example 2

Preparation of Doxepin Isomer

Five grams of the cis/trans mixture of doxepin hydrochloride is converted to the free base and then to the maleate salt, M.P. 168-169° C. Several recrystallizations from ethanol afford a pure isomeric maleate, M.P. 172-173° C. This is reconverted to the free base and then to the hydrochloric acid-addition salt. This is purified by recrystallization from a mixture of ethanol and ether; M.P. 192-193° C. The other pure isomer is isolated by the concentration of the crystallization liquors to dryness, followed by converting the residue to the free base and then converting the base to the hydrochloric-acid addition salt. After recrystallization from a mixture of ethanol and ether, the salt has a M.P. of 209-210.5° C.

Example 3

Preparation of Desmethyldoxepin

Desmethyldoxepin is prepared according to the following method. Anhydrous 3-methylaminopropyltriphenylphosphonium bromide hydrobromide (1530 g) prepared as in U.S. Pat. No. 3,509,175, is suspended in 4.5 l dry tetrahydrofuran and 6.0 moles of butyl lithium in heptane is added during 1 hour. After an additional 30 minutes, 483 g of 6,11-dihydrodibenz(b,e)oxepin-11-one, is added to the deep red solution and the reaction is maintained at reflux for 10 hours. Water, 500 ml, is added at room temperature and the solvent is removed in vacuo. The crude residue is treated with 10% hydrochloric acid until acidic (pH 2) and then 1.5 l benzene is added. After stirring, the mixture separates into three phases (an insoluble hydrochloride salt product phase, an aqueous phase and an organic phase). The benzene layer is removed by decantation and the remaining mixture is rendered basic with 10% sodium hydroxide solution and is extracted with 3×1500 ml portions of benzene. The benzene extracts are washed, then dried with anhydrous sodium sulfate and concentrated in a vacuum leaving a solid residue of desmethyldoxepin.

Example 4

Preparation of (e)-desmethyldoxepin (E)-Desmethyldoxepin is prepared from doxepin hydrochloride as follows. Doxepin hydrochloride (E/Z=85/15) (55.0 g, 0.174 mol) is dissolved in 600 mL $H_2O$, made basic with 6M NaOH, and extracted with $CHCl_3$ (3×600 mL). The $CHCl_3$ extracts are combined, dried over $Na_2SO_4$, and solvent removed in vacuo. The resulting oil is dissolved in 250 mL EtOH, then 21.15 g (0.182 mol) of maleic acid dissolved in 100 mL EtOH is added slowly, with stirring, followed by an additional 350 mL EtOH. The resulting cloudy solution is refluxed until it becomes clear, then allowed to stand overnight at room temperature; the resulting crystals are isolated by vacuum filtration. Additional recrystallization from EtOH yields a white crystalline product ((E)-Doxepin maleate) with an E/Z ratio of 98/2. (E)-Doxepin maleate (2.50 g, 6.32 mmol) is then partially dissolved in 60 mL H2O, made basic with 6M NaOH, and extracted with CHCl3 (3×60 mL). The CHCl3 extracts are combined, washed with 60 mL brine, dried over Na2SO4, and solvent removed in vacuo. The resulting oil is re-dissolved in 10 mL CHCl3, 1.8 mL (13 mmol) of triethylamine added, 1.8 mL (13 mmol) of 2,2,2-trichloroethyl-chloro-formate added, and reaction stirred under N2 for 3.5 hours. The completed reaction is then diluted with 140 mL Et2O, washed successively with 0.5M HCl (2×140 mL), H2O (140 mL), and brine (140 mL), then dried over MgSO4 and solvent removed in vacuo. Resulting material is further purified by silica gel column chromatography, eluting with EtOAc/Hex (20/80), to afford 1.48 g (3.36 mmol) of the desired product as a clear oil. The N-protected (E)-desmethyldoxepin intermediate (1.44 g, 3.27 mmol) is then dissolved in 12 mL THF, 2.88 g of zinc powder added, 2.3 mL of 1M sodium phosphate (pH=5.5) added, and reaction stirred for 17 hours. The reaction mixture is then vacuum filtered, filtrate solvent removed in vacuo, and resulting residue purified by silica gel column chromatography, eluting with THF/MeOH/NH$_4$OH (85/15/0.4), then THF/MeOH/NH$_4$OH (75/25/0.4), to afford 744 mg (2.80 mmol) of the desired product as a pale yellow solid.

Example 5

Preparation of (z)-desmethyl doxepin (Z)-Desmethyldoxepin is prepared from doxepin hydrochloride as follows. Doxepin hydrochloride (E/Z=85/15) (100 g, 0.317 mol) is dissolved in 800 mL H$_2$O, made basic with 6M NaOH, and extracted with CHCl$_3$ (3×800 mL). The CHCl$_3$ extracts are combined, dried over Na$_2$SO$_4$, and solvent removed in vacuo. The resulting oil is dissolved in 700 mL EtOH, then 36.7 g (0.317 mol) of maleic acid dissolved in 600 mL EtOH is added slowly, with stirring. The resulting cloudy solution is refluxed until clear, then allowed to stand overnight at room temperature. Crystals are isolated by vacuum filtration and the mother liquor saved. Crystals are recrystallized two additional times as above, and the three mother liquors saved and combined and solvent removed in vacuo. Recrystallization of mother liquor material from refluxing EtOH eventually affords 24 g of a mother liquor product which is 65% Z isomer in composition. Recrystallization of this material from 450 mL EtOH gives crystals (9.1 g) which are 80% Z isomer. This material is recrystallized from 170 mL CHCl$_3$/CCl$_4$ (50/50) at 4° C., yielding 7.65 g of crystalline material which is 87% Z isomer in composition. Three additional recrystallizations from CHCl$_3$/CCl$_4$ eventually affords 5.12 g (12.9 mmol) of the desired product ((Z)-Doxepin maleate) with an E/Z ratio of 4/96; melting point: 162°-163° C. (Z)-Doxepin maleate (1.00 g, 2.53 mmol) is then partially dissolved in 35 mL H$_2$O, made basic with 6M NaOH, and extracted with CHCl$_3$ (3×35 mL). The CHCl$_3$ extracts are combined, washed with 35 mL brine, dried over Na$_2$SO$_4$, and solvent removed in vacuo. The resulting oil is re-dissolved in 4 mL CHCl$_3$, 0.65 mL (4.7 mmol) of triethylamine added, 0.65 mL (4.7 mmol) of 2,2,2-trichloroethyl-chloroformate added, and reaction stirred under N$_2$ for 3.5 hours. The completed reaction is then diluted with 50 mL Et$_2$O, washed successively with 0.5M HCl (2×50 mL), H$_2$O (50 mL), and brine (50 mL), then dried over MgSO$_4$ and solvent removed in vacuo. Resulting material is further purified by silica gel column chromatography, eluting with EtOAc/Hex (20/80), to afford 710 mg (1.61 mmol) of the desired product as a clear oil. The N-protected (Z)-desmethyldoxepin (679 mg, 1.54 mmol) is then dissolved in 5.7 mL THF, 1.36 g of zinc powder added, 1.1 mL of 1M sodium phosphate (pH=5.5) added, and reaction stirred for 17 hours. The reaction mixture is then vacuum filtered, filtrate solvent removed in vacuo, and resulting residue purified by silica gel column chromatography, eluting with THF/MeOH/NH$_4$OH (85/15/0.4), then THF/MeOH/NH$_4$OH (82/18/0.4), to afford 364 mg (1.37 mmol) of the desired product as a pale yellow solid.

Example 6

Preparation of (Z)-2-Hydroxy-11-(3-dimethylamino-propylidene)-6,11-dihydrodibenzo [b,e]oxepin A mixture of 2-methoxy-11-(3-dimethylaminopropyl)-6,11-dihydrodibenzo[b,e]oxepin (165 mg, 0.005 mol) with glacial acetic acid (0.2 ml) and hydriodic acid (0.2 ml, 57%) was stirred and heated for 5 hr at 90° C. The product was then extracted and purified by pouring into ice water (25 ml), made alkaline with sodium hydroxide (2N) and extracted with ether (2×10 ml). The aqueous layer was then adjusted to pH 6.8 with hydrochloric acid (6N). The mixture was then brought to pH 7 by the addition of sodium bicarbonate solution (5%) and extracted with chloroform (2×10 ml). The extract was dried over anhydrous sodium sulfate and evaporated in vacuo to give a yellowish solid. The crude reaction product was purified by preparative TLC (chloroform/toluene/methanol/ammonia, 4:3:2:1, v/v).

Example 7

Preparation of (E)-2-Hydroxy-11-(3-dimethylamino-propylidene)-6,11-dihydrodibenzo[b,e]oxepin A mixture of (Z)-2-Hydroxy-11-(3-dimethylaminopropylidene)-6,11-dihydrodibenzo[b,e]oxepin (2.5 mg, 8.5×10$^{-6}$ mol) was dissolved in a mixture of hydrochloric acid (1 ml) and methanol (9 ml) and heated at 140° C. (oil bath) for 4 hr. The product was isolated by means of HPLC and evaporation of solvents.

Example 8

Preparation of (Z)-2-Hydroxy-11-(3-methylamino-propylidene)-6,11-dihydrodibenzo[b,e]oxepin A mixture of 2-methoxy-11-(3-methylaminopropyl)-6,11-dihydrodibenzo[b,e]oxepin (0.005 mol) with glacial acetic acid (0.2 ml) and hydriodic acid (0.2 ml, 57%) is stirred and heated for 5 hr at 90° C. The product is then extracted and purified by pouring into ice water (25 ml), made alkaline with sodium hydroxide (2N) and extracted with ether (2×10 ml). The aqueous layer is then adjusted to pH 6.8 with hydrochloric acid (6N). The mixture is then brought to pH 7 by the addition of sodium bicarbonate solution (5%) and extracted with chloroform (2×10 ml). The extract is dried over anhydrous sodium sulfate and evaporated in vacuo to give a yellowish solid. The crude reaction product is purified by preparative TLC (chloroform/toluene/methanol/ammonia, 4:3:2:1, v/v).

Example 9

Preparation of (E)-2-Hydroxy-11-(3-methylaminopropylidene)-6,11-dihydrodibenzo[b,e]oxepin A mixture of (Z)-2-Hydroxy-11-(3-methylaminopropylidene)-6,11-dihydrodibenzo [b,e]oxepin (2.5 mg) is dissolved in a mixture of hydrochloric acid (1 ml) and methanol (9 ml) and heated at 140° C. (oil bath) for 4 hr. The product is isolated by means of HPLC and evaporation of solvents.

Example 10

Preparation of doxepin-N-oxide

An aqueous solution of doxepin hydrochloride was made alkaline and extracted with methylene chloride. Solvent was removed and the residue, dissolved in methanol, was treated for 5 days with an excess of 30% hydrogen peroxide. Chromatographic examination indicated that the doxepin had been completely replaced by a more polar substance determined from its mass spectrum to be the N-oxide.

Hobbs, D. C., Distribution and Metabolism of Doxepin (1969) Biochem Pharmacol 18:1941-1954; which is incorporated herein by reference in its entirety.

Example 11

Preparation of (Z) doxepin-N-oxide

An aqueous solution of purified (Z)-doxepin hydrochloride is made alkaline and extracted with methylene chloride. Solvent is removed and the residue, dissolved in methanol, is treated for 5 days with an excess of 30% hydrogen peroxide. Chromatographic examination indicates that the doxepin has been completely replaced by a more polar substance determined from its mass spectrum to be the N-oxide of the (Z) isomer of doxepin.

Example 12

Preparation of (E) doxepin-N-oxide

An aqueous solution of purified (E)-doxepin hydrochloride is made alkaline and extracted with methylene chloride. Solvent is removed and the residue, dissolved in methanol, is treated for 5 days with an excess of 30% hydrogen peroxide. Chromatographic examination indicates that the doxepin has been completely replaced by a more polar substance determined from its mass spectrum to be the N-oxide of the (E) isomer of doxepin.

Example 13

Isolation of (E)-N-acetyl-N-desmethyldoxepin, (E)-N-desmethyl-N-formyldoxepin, and (E)-N-acetyldidesmethyldoxepin)

(E)-N-acetyl-N-desmethyldoxepin, (E)-N-desmethyl-N-formyldoxepin, and (E)-N-acetyldidesmethyldoxepin are isolated from *Cunninghamella elegans* (*C. elegans*) as described in the incorporated materials of Moody et al. (Drug Metabolism and Disposition (1999) 27:1157-1164). Briefly, cultures of *C. elegans* ATCC 9245 are incubated for 48 h at 26° C. on a rotary shaker operating at 125 rpm and then 10 mg of doxepin hydrochloride (E./Z ratio 83:16%) dissolved in 0.5 ml sterile physiological saline solution are added. After 96 h of incubation, the contents of each flask, are filtered through glass wool into a separatory funnel and extracted with three equal volumes of ethyl acetate. The organic extracts are dried over sodium sulfate and evaporated to dryness in vacuo at 34°. The residue is dissolved in methanol and concentrated to approximately 100 μL by evaporation for analysis by HPLC.

The extract is injected repeatedly into a semipreparative scale HPLC system consisting of a Beckman model 100A pump, a Waters 486 turntable UV absorbance detector, and a Shimadzu model CR601 Chromatopac integrator. The compounds are eluted using a linear gradient of 30 to 75% methanol-buffer (v/v) over 30 min at 1.0 ml/min with a 10.0×250 mm column. The buffer used is 25 mM ammonium acetate, pH 7.2. Compounds with similar retention times are pooled. NMR and mass spectral analysis confirms the isolation of (E)-N-acetyl-N-desmethyldoxepin, (E)-N-desmethyl-N-formyldoxepin, and (E)-N-acetyldidesmethyldoxepin.

Example 14

Isolation of (Z)—N-acetyl-N-desmethyldoxepin, (Z)—N-desmethyl-N-formyldoxepin, and (Z)—N-acetyldidesmethyldoxepin (Z)—N-acetyl-N-desmethyldoxepin, (Z)—N-desmethyl-N-formyldoxepin, and (Z)—N-acetyldidesmethyldoxepin are isolated from *Cunninghamella elegans* (*C. elegans*) as described above in Example 12 for the (E) isomers. However, unlike Example 13, the cultures are initially incubated with doxepin enriched for the cis (Z)-isomer of doxepin at a Z/E ratio of greater than 85:15. NMR and mass spectral analysis confirms the isolation of (Z)—N-acetyl-N-desmethyldoxepin, (Z)—N-desmethyl-N-formyldoxepin, and (Z)—N-acetyldidesmethyldoxepin.

Example 15

Isolation of (E)- and (Z)—N-didesmethyldoxepin (E)- and (Z)—N-didesmethyldoxepin are isolated from blood serum and cerebrospinal fluid of patients treated with doxepin according to the methods described in the incorporated materials of Deuschle et al. (Psychopharmacology (1997) 131:19-22). Briefly, blood and cerebrospinal fluid are collected from patients being treated with doxepin. After centrifugation, (15000 g for 5 min), 100 μl of the samples is injected directly onto a clean-up column (10.0×4.0 mm) filled with Lichrospher RP-8 DIOL. Interfering plasma or CSF constituents are washed to waste using water containing 5% acetonitrile at a flow rate of 1.5 ml/min. After 5 min the flow is switched onto an analytical column and the drugs of interest are separated using methanol: acetonitrile: 0.008M phosphate buffer, pH 6.4 (188:578:235; V/V) for elution. NMR and mass spectral analysis confirms the isolation of (E)-N-didesmethyldoxepin and (Z)—N-didesmethyldoxepin.

Example 16

Isolation of (E)-2-O-glucuronyldoxepin and (E)-3-O-glucuronyldoxepin (E)-2-O-glucuronyldoxepin and (E)-3-O-glucuronyldoxepin are isolated from rat bile according to the methods described in the incorporated materials of Shu et al. (Drug Metabolism and Disposition (1990)18:1096-1099). Briefly, samples of rat bile are collected from rats for 4 hours after intraperitoneal injection with doxepin hydrochloride (28 mg/kg). The samples are chromatographed on a gradient HPLC system that consists of two solvent delivery pumps (Waters M045), a system controller (Waters Model 720), a UV absorbance detector (Waters Model 441), and an integrator (Hewlett 3390A). Chromotography is carried out on a column packed with Spherisorb nitrile (3 μm, 0.46×15 cm) and maintained at 50° C. The analysis begins with an initial isocratic period (1 min) with 95% solvent A (water) and 5% solvent B (acetonitrile/methanol, 75:25, v/v). Thereafter, a linear gradient elution is established by increasing the proportion of solvent B from 5% to 100% from 1 to 16 min, followed by a final period (4 min) of isocratic elution with 100% solvent B. The flow rate is 1.5 ml/min and UV absorbance is monitored at 254 nm with a sensitivity of 0.005 AUFS. NMR and mass spectral analysis confirms the isolation of (E)-2-O-glucuronyldoxepin and (E)-3-O-glucuronyldoxepin.

Example 17

Isolation of (Z)-2-O-glucuronyldoxepin and (Z)-3-O-glucuronyldoxepin (Z)-2-O-glucuronyldoxepin and (Z)-3-O-glucuronyldoxepin are isolated from rat bile according to the methods described above in Example 16 with the exception that the rats are injected with doxepin enriched for the cis (Z)-isomer of doxepin at a Z/E ratio of greater than 85:15. NMR and mass spectral analysis confirms the isolation of (Z)-2-O-glucuronyldoxepin and (Z)-3-O-glucuronyldoxepin.

Example 18

Preparation of (E)- and (Z)-doxepin $N^+$-glucuronide

The quaternary ammonium-linked glucuronide of doxepin (doxepin $N^+$-glucuronide) is obtained by organic synthesis as described in the incorporated materials of Luo et al. (Drug Metabolism and Disposition, (1991) 19:722-724). Briefly, the synthetic procedure involves quaternization of commercial samples of doxepin with methyl(2,3,4-tri-O-acetyl-1-bromo-1-deoxy-α-D-glucopyranosid)urinate, and subsequent removal of the protecting groups by treatment with sodium hydroxide. Thus, to prepare the (Z)-isomer of doxepin $N^+$-glucuronide, (Z)-doxepin is used as the starting material. To prepare the (E)-isomer of doxepin, (E)-doxepin is used as the starting material.

Example 19

The patient suffers from transient or short-term insomnia. At the time of consultation, he is otherwise healthy with normal affect with no depression, anxiety or substance overuse. He is prescribed a mixture of cis-(Z) and trans-(E) isomers of doxepin or a doxepin metabolite containing greater than 18.1% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has him sleeping well.

Example 20

The patient suffers from transient or short-term insomnia. At the time of consultation, he is otherwise healthy with normal affect with no depression, anxiety or substance overuse. He is prescribed a mixture of cis-(Z) and trans-(E) isomers of doxepin or a doxepin metabolite containing greater than 20% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has him sleeping well.

Example 21

The patient suffers from transient or short-term insomnia. At the time of consultation, he is otherwise healthy with normal affect with no depression, anxiety or substance overuse. He is prescribed a mixture of cis-(Z) and trans-(E) isomers of doxepin or a doxepin metabolite containing greater than 30% and less than 99.5% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has him sleeping well.

Example 22

The patient suffers from transient or short-term insomnia. At the time of consultation, he is otherwise healthy with normal affect with no depression, anxiety or substance overuse. He is prescribed the cis-(Z) isomer of doxepin or a doxepin metabolite in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the doxepin isomer relieves the insomnia and has him sleeping well.

Example 23

The patient suffers from transient or short-term insomnia. At the time of consultation, she also suffers from depression. She is prescribed a mixture of cis-(Z) and trans-(E) isomers of doxepin or a doxepin metabolite containing greater than 18.1% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has her sleeping well.

Example 24

The patient suffers from transient or short-term insomnia. At the time of consultation, she also suffers from depression. She is prescribed a mixture of cis-(Z) and trans-(E) isomers of doxepin or a doxepin metabolite containing greater than 20% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has her sleeping well.

Example 25

The patient suffers from transient or short-term insomnia. At the time of consultation, she also suffers from depression.

She is prescribed a mixture of cis-(Z) and trans-(E) isomers of doxepin or a doxepin metabolite containing greater than 30% and less than 99.5% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has her sleeping well.

Example 26

The patient suffers from transient or short-term insomnia. At the time of consultation, she also suffers from depression. She is prescribed the cis-(Z) isomer of doxepin or a doxepin metabolite in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the doxepin isomer relieves the insomnia and has her sleeping well.

Example 27

The patient suffers from chronic insomnia. At the time of consultation, he is otherwise healthy with normal affect with no depression, anxiety or substance abuse. He is prescribed a mixture of cis-(Z) and trans-(E) isomers of doxepin or a doxepin metabolite containing greater than 18.1% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has him sleeping well.

Example 28

The patient suffers from chronic insomnia. At the time of consultation, he is otherwise healthy with normal affect with no depression, anxiety or substance abuse. He is prescribed a mixture of cis-(Z) and trans-(E) isomers of doxepin or a doxepin metabolite containing greater than 20% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has him sleeping well.

Example 29

The patient suffers from chronic insomnia. At the time of consultation, he is otherwise healthy with normal affect with no depression, anxiety or substance abuse. He is prescribed a mixture of cis-(Z) and trans-(E) isomers of doxepin or a doxepin metabolite containing greater than 30% and less than 99.5% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has him sleeping well.

Example 30

The patient suffers from chronic insomnia. At the time of consultation, he is otherwise healthy with normal affect with no depression, anxiety or substance abuse. He is prescribed the cis-(Z) isomer of doxepin or a doxepin metabolite in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the doxepin isomer relieves the insomnia and has him sleeping well.

Example 31

The patient suffers from chronic insomnia. At the time of consultation, she also suffers from depression. She is prescribed a mixture of cis-(Z) and trans-(E) isomers of doxepin or a doxepin metabolite containing greater than 18.1% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has her sleeping well.

Example 32

The patient suffers from chronic insomnia. At the time of consultation, she also suffers from depression. She is prescribed a mixture of cis-(Z) and trans-(E) isomers of doxepin or a doxepin metabolite containing greater than 20% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has her sleeping well.

Example 33

The patient suffers from chronic insomnia. At the time of consultation, she also suffers from depression. She is prescribed a mixture of cis-(Z) and trans-(E) isomers of doxepin or a doxepin metabolite containing greater than 30% and less than 99.5% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has her sleeping well.

Example 34

The patient suffers from chronic insomnia. At the time of consultation, she also suffers from depression. She is prescribed the cis-(Z) isomer of doxepin or a doxepin metabolite in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the doxepin isomer relieves the insomnia and has her sleeping well.

Example 35

The patient suffers from maintenance (non-chronic) insomnia. At the time of consultation, he is otherwise healthy with normal affect with no depression, anxiety or substance overuse. He is prescribed a mixture of cis-(Z) and trans-(E) isomers of doxepin or a doxepin metabolite containing greater than 18.1% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has him sleeping well.

Example 36

The patient suffers from maintenance (non-chronic) insomnia. At the time of consultation, he is otherwise healthy with normal affect with no depression, anxiety or substance overuse. He is prescribed a mixture of cis-(Z) and trans-(E) isomers of doxepin or a doxepin metabolite containing greater than 20% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has him sleeping well.

Example 37

The patient suffers from maintenance (non-chronic) insomnia. At the time of consultation, he is otherwise healthy with normal affect with no depression, anxiety or substance overuse. He is prescribed a mixture of cis-(Z) and trans-(E) isomers of doxepin or a doxepin metabolite containing greater than 30% and less than 99.5% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has him sleeping well.

Example 38

The patient suffers from maintenance (non-chronic) insomnia. At the time of consultation, he is otherwise healthy with normal affect with no depression, anxiety or substance overuse. He is prescribed the cis-(Z) isomer of doxepin or a doxepin metabolite in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the doxepin isomer relieves the insomnia and has him sleeping well.

Example 39

The patient suffers from maintenance (chronic) insomnia. At the time of consultation, he is otherwise healthy with normal affect with no depression, anxiety or substance abuse. He is prescribed a mixture of cis-(Z) and trans-(E) isomers of doxepin or a doxepin metabolite containing greater than 88.2% trans-(E) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has him sleeping well.

Example 40

The patient suffers from maintenance (chronic) insomnia. At the time of consultation, he is otherwise healthy with normal affect with no depression, anxiety or substance abuse. He is prescribed a mixture of cis-(Z) and trans-(E) isomers of doxepin or a doxepin metabolite containing greater than 90% trans-(E) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has him sleeping well.

Example 41

The patient suffers from maintenance (chronic) insomnia. At the time of consultation, he is otherwise healthy with normal affect with no depression, anxiety or substance abuse. He is prescribed a mixture of cis-(Z) and trans-(E) isomers of doxepin or a doxepin metabolite containing greater than 90% and less than 99.5% trans-(E) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has him sleeping well.

Example 42

The patient suffers from maintenance (chronic) insomnia. At the time of consultation, he is otherwise healthy with normal affect with no depression, anxiety or substance abuse. He is prescribed the trans-(E) isomer of doxepin or a doxepin metabolite in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the doxepin isomer relieves the insomnia and has him sleeping well.

Example 43

The patient suffers from onset (non-chronic) insomnia. At the time of consultation, she is otherwise healthy with normal affect with no depression, anxiety or substance abuse. She is prescribed a mixture of cis-(Z) and trans-(E) isomers of doxepin or a doxepin metabolite containing greater than 18.1% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has her sleeping well.

Example 44

The patient suffers from onset (non-chronic) insomnia. At the time of consultation, she is otherwise healthy with normal affect with no depression, anxiety or substance abuse. She is prescribed a mixture of cis-(Z) and trans-(E) isomers of doxepin or a doxepin metabolite containing greater than 20% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has her sleeping well.

Example 45

The patient suffers from onset (non-chronic) insomnia. At the time of consultation, she is otherwise healthy with normal affect with no depression, anxiety or substance abuse. She is prescribed a mixture of cis-(Z) and trans-(E) isomers of doxepin or a doxepin metabolite containing greater than 30% and less than 99.5% cis-(Z) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has her sleeping well.

Example 46

The patient suffers from onset (non-chronic) insomnia. At the time of consultation, she is otherwise healthy with normal affect with no depression, anxiety or substance abuse. She is prescribed the cis-(Z) isomer of doxepin or a doxepin metabolite in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the doxepin isomer relieves the insomnia and has her sleeping well.

Example 47

The patient suffers from onset (chronic) insomnia. At the time of consultation, she is otherwise healthy with normal affect with no depression, anxiety or substance abuse. She is prescribed a mixture of cis-(Z) and trans-(E) isomers of doxepin or a doxepin metabolite containing greater than 88.2% trans-(E) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has her sleeping well.

Example 48

The patient suffers from onset (chronic) insomnia. At the time of consultation, she is otherwise healthy with normal affect with no depression, anxiety or substance abuse. She is prescribed a mixture of cis-(Z) and trans-(E) isomers of doxepin or a doxepin metabolite containing greater than 90% trans-(E) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has her sleeping well.

Example 49

The patient suffers from onset (chronic) insomnia. At the time of consultation, she is otherwise healthy with normal affect with no depression, anxiety or substance abuse. She is prescribed a mixture of cis-(Z) and trans-(E) isomers of doxepin or a doxepin metabolite containing greater than 90% and less than 99.5% trans-(E) isomer in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the specified isomeric mixture of doxepin relieves the insomnia and has her sleeping well.

Example 50

The patient suffers from onset (chronic) insomnia. At the time of consultation, she is otherwise healthy with normal affect with no depression, anxiety or substance abuse. She is prescribed the trans-(E) isomer of doxepin or a doxepin metabolite in a daily dosage of 0.0001 milligram, 0.1 milligram, 1 milligram, 3 milligrams, 6 milligrams, 10 milligrams, 20 milligrams or 40 milligrams, taken prior to bedtime. Follow up reveals that the administration of the doxepin isomer relieves the insomnia and has her sleeping well.

Example 51

The patient suffers from a sleep disorder. The patient is prescribed a mixture of cis-(Z) and trans-(E) isomers of a pharmaceutically-acceptable salt of doxepin or a doxepin metabolite containing greater than 18.1% cis-(Z) isomer in a daily dosage of 1 milligram, 2 milligrams, 3 milligrams, 6 milligrams, 10 milligrams, 20 milligrams or 40 milligrams, taken prior to bedtime. Follow up reveals that the administration of the specified isomeric mixture of the doxepin salt relieves the insomnia and has him sleeping well.

Example 52

The patient suffers from a sleep disorder. The patient is prescribed a mixture of cis-(Z) and trans-(E) isomers of a pharmaceutically-acceptable salt of doxepin or a doxepin metabolite containing greater than 20% cis-(Z) isomer in a daily dosage of 1 milligram, 2 milligrams, 3 milligrams, 6 milligrams, 10 milligrams, 20 milligrams or 40 milligrams, taken prior to bedtime. Follow up reveals that the administration of the specified isomeric mixture of the doxepin salt relieves the insomnia and has him sleeping well.

Example 53

The patient suffers from a sleep disorder. The patient is prescribed a mixture of cis-(Z) and trans-(E) isomers of a pharmaceutically-acceptable salt of doxepin or a doxepin metabolite containing greater than 30% and less than 99.5% cis-(Z) isomer in a daily dosage of 1 milligram, 2 milligrams, 3 milligrams, 5 milligrams, 6 milligrams, 10 milligrams, 20 milligrams or 40 milligrams, taken prior to bedtime. Follow up reveals that the administration of the specified isomeric mixture of the doxepin salt relieves the insomnia and has him sleeping well.

Example 54

The patient suffers from a sleep disorder. The patient is prescribed the cis-(Z) isomer of a pharmaceutically-acceptable salt of doxepin or a doxepin metabolite in a daily dosage of 1 milligram, 2 milligrams, 3 milligrams, 5 milligrams, 6 milligrams, 10 milligrams, 20 milligrams or 40 milligrams, taken prior to bedtime. Follow up reveals that the administration of the isomer of the doxepin salt relieves the insomnia and has him sleeping well.

Example 55

The patient suffers from a sleep disorder. The patient is prescribed a mixture of cis-(Z) and trans-(E) isomers of a prodrug of doxepin or a doxepin metabolite containing greater than 18.1% cis-(Z) isomer in a daily dosage of 1 milligram, 2 milligrams, 3 milligrams, 5 milligrams, 6 milligrams, 10 milligrams, 20 milligrams or 40 milligrams, taken prior to bedtime. Follow up reveals that the administration of the specified isomeric mixture of the doxepin prodrug relieves the insomnia and has him sleeping well.

Example 56

The patient suffers from a sleep disorder. The patient is prescribed a mixture of cis-(Z) and trans-(E) isomers of a prodrug salt of doxepin or a doxepin metabolite containing greater than 20% cis-(Z) isomer in a daily dosage of 1 milligram, 2 milligrams, 3 milligrams, 5 milligrams, 6 milligrams, 10 milligrams, 20 milligrams or 40 milligrams, taken prior to bedtime. Follow up reveals that the administration of the specified isomeric mixture of the doxepin prodrug relieves the insomnia and has him sleeping well.

Example 57

The patient suffers from a sleep disorder. The patient is prescribed a mixture of cis-(Z) and trans-(E) isomers of a prodrug of doxepin or a doxepin metabolite containing greater than 30% and less than 99.5% cis-(Z) isomer in a daily dosage of 1 milligram, 2 milligrams, 3 milligrams, 5 milligrams, 6 milligrams, 10 milligrams, 20 milligrams or 40 milligrams, taken prior to bedtime. Follow up reveals that the administration of the specified isomeric mixture of the doxepin prodrug relieves the insomnia and has him sleeping well.

Example 58

The patient suffers from a sleep disorder. The patient is prescribed the cis-(Z) isomer of a prodrug of doxepin or a doxepin metabolite in a daily dosage of 1 milligram, 2 milligrams, 3 milligrams, 5 milligrams, 6 milligrams, 10 milligrams, 20 milligrams or 40 milligrams, taken prior to bedtime. Follow up reveals that the administration of the isomer of the doxepin prodrug relieves the insomnia and has him sleeping well.

Many modifications and variations of the embodiments described herein may be made without departing from the scope, as is apparent to those skilled in the art. The specific embodiments described herein are offered by way of example only.

What is claimed is:

1. A method for the treatment of a patient suffering from sleep maintenance insomnia characterized by fragmented sleep during the $8^{th}$ hour of sleep, comprising:
    identifying a patient having a sleep disorder in which, for a given 8 hour period of desired sleep, the patient experiences fragmented sleep during the final 60 minutes of said period; and
    administering to said patient, prior to the start of the sleep period, a dosage of doxepin or a pharmaceutically-acceptable salt thereof that is effective to improve sleep maintenance insomnia by reducing early awakenings during the $8^{th}$ hour of the sleep period, wherein the dosage ranges from about 0.1 to about 20 milligrams, wherein the doxepin or salt thereof is a geometric isomer mixture containing about 18.2% to about 100.0% of the cis-(Z) isomer or is 100% cis-(Z) isomer.

2. The method of claim 1, wherein said geometric isomer mixture contains more than 20% of the cis-(Z) isomer.

3. The method of claim 1, wherein said geometric isomer mixture contains more than 50% of the cis-(Z) isomer.

4. The method of claim 1, wherein said geometric isomer mixture contains more than 90% of the cis-(Z) isomer.

5. The method of claim 1, wherein said geometric isomer mixture contains more than 95% of the cis-(Z) isomer.

6. The method of claim 1, wherein said geometric isomer mixture contains about 20% to about 99.9% of the cis-(Z) isomer.

7. The method of claim 1, wherein the dosage is about 1 to about 6 milligrams.

8. A method for the treatment of a patient suffering from sleep maintenance insomnia characterized by early awakenings during the $8^{th}$ hour of sleep, comprising:
    identifying a patient having a sleep disorder in which, for a given 8 hour period of desired sleep, the patient experiences early awakenings during the final 60 minutes of said period; and
    administering to said patient, prior to the start of the sleep period, a dosage of doxepin or a pharmaceutically-acceptable salt thereof that is effective to improve sleep maintenance insomnia by reducing early awakenings during the $8^{th}$ hour of the sleep period, wherein the dosage ranges from about 0.1 to about 20 milligrams, wherein the doxepin or salt thereof is a geometric isomer mixture containing about 18.2% to about 100.0% of the cis-(Z) isomer or is 100% cis-(Z) isomer.

9. The method of claim 8, wherein said geometric isomer mixture contains more than 20% of the cis-(Z) isomer.

10. The method of claim 8, wherein said geometric isomer mixture contains more than 50% of the cis-(Z) isomer.

11. The method of claim 8, wherein said geometric isomer mixture contains more than 90% of the cis-(Z) isomer.

12. The method of claim 8, wherein said geometric isomer mixture contains more than 95% of the cis-(Z) isomer.

13. The method of claim 8, wherein said geometric isomer mixture contains about 20% to about 99.9% of the cis-(Z) isomer.

14. The method of claim 8, wherein the dosage is about 1 to about 6 milligrams.

* * * * *